(12) United States Patent
Nishikawa et al.

(10) Patent No.: US 10,266,601 B2
(45) Date of Patent: Apr. 23, 2019

(54) RECOMBINANT OBLIGATE ANAEROBIC GRAM-POSITIVE BACTERIA

(71) Applicant: TEIKYO HEISEI UNIVERSITY, Tokyo (JP)

(72) Inventors: Takeshi Nishikawa, Chiba (JP); Yuichiro Taira, Tokyo (JP); Ikuko Taira, Tokyo (JP); Isao Ishida, Kanagawa (JP)

(73) Assignee: TEIKYO HEISEI UNIVERSITY, Tokyo (JP)

( * ) Notice: Subject to any disclaimer, the term of this patent is extended or adjusted under 35 U.S.C. 154(b) by 228 days.

(21) Appl. No.: 15/110,131

(22) PCT Filed: Dec. 24, 2014

(86) PCT No.: PCT/JP2014/084038
§ 371 (c)(1),
(2) Date: Jul. 7, 2016

(87) PCT Pub. No.: WO2015/104994
PCT Pub. Date: Jul. 16, 2015

(65) Prior Publication Data
US 2016/0326256 A1    Nov. 10, 2016

(30) Foreign Application Priority Data
Jan. 10, 2014 (JP) .................................. 2014-003441

(51) Int. Cl.
| C07K 16/00 | (2006.01) |
| C07K 16/28 | (2006.01) |
| A61K 35/74 | (2015.01) |
| C12N 15/74 | (2006.01) |
| A61K 39/00 | (2006.01) |

(52) U.S. Cl.
CPC .......... *C07K 16/2878* (2013.01); *A61K 35/74* (2013.01); *C12N 15/746* (2013.01); *A61K 2039/505* (2013.01); *A61K 2039/54* (2013.01); *C07K 2317/14* (2013.01); *C07K 2317/565* (2013.01); *C07K 2317/569* (2013.01); *C07K 2317/622* (2013.01); *C07K 2317/76* (2013.01); *C07K 2317/92* (2013.01); *C07K 2319/00* (2013.01); *C07K 2319/02* (2013.01)

(58) Field of Classification Search
None
See application file for complete search history.

(56) References Cited

U.S. PATENT DOCUMENTS

| 2011/0190472 A1* | 8/2011 | Shimatani-Shibata ..................... C12N 15/746 530/300 |
| 2011/0318366 A1* | 12/2011 | Cromie .............. C07K 16/2878 424/172.1 |
| 2015/0191706 A1 | 7/2015 | Taira et al. |

FOREIGN PATENT DOCUMENTS

| JP | 2013519364 A | 5/2013 |
| WO | 2009030285 A1 | 3/2009 |
| WO | 2010126073 A1 | 11/2010 |
| WO | 2011098520 A1 | 8/2011 |
| WO | 2014010758 A1 | 1/2014 |

OTHER PUBLICATIONS

Micheau et al., "Death receptors as targets in cancer", Br. J. Pharmacol., 2013, vol. 169, No. 8, pp. 1723-1744.
Ghobrial et al., "Targeting Apoptosis Pathways in Cancer Therapy", CA. Cancer J. Clin., 2005, vol. 55, No. 3, pp. 178-194.
Motoki et al., "Enhanced Apoptosis and Tumor Regression Induced by a Direct Agonist Antibody to Tumor Necrosis Factor-Related Apoptosis-Inducing Ligand Receptor 2", Clin. Cancer Res., 2005, vol. 11, No. 8, pp. 3126-3135.
Jo et al., "Apoptosis induced in normal human hepatocytes by tumor necrosis factor-related apoptosis-inducing ligand", Nat. Med., 2000, vol. 6, No. 5, pp. 564-567.
Mori et al., "Human normal hepatocytes are susceptible to apoptosis signal mediated by both TRAIL-R1 and TRAIL-R2", Cell Death Differ., 2004, vol. 11, No. 2, pp. 203-207.
International Search Report for International Application No. PCT/JP2014/084038 (dated Apr. 7, 2015)(4 Pages).
Dobson et al., "Human monomeric antibody fragments to TRAIL-R1 and TRAIL-R2 that display potent in vitro agonism", MABS, 2009, vol. 1, No. 6, pp. 552-562.
Anne et al., "Protein secretion biotechnology in Gram-positive bacteria with special emphasis on Streptomyces lividian", Biochimica Et Biophysica Acta., 2014, vol. 1843, No. 8, pp. 1750-1761.
Groot et al., "Functional antibodies produced by oncolytic clostridia" Biochemical and Biophysical Research Communications, 2007, vol. 364, No. 4, pp. 985-989.
Cronin et al.,"Orally Administered Bifidobacteria as Vehicles for Delivery of Agents to Systemic Tumors", Molecular Therapy, 2010, vol. 18, No. 7, pp. 1397-1407.
Takeda et al., "Targeting death-inducing receptors in cancer therapy", Oncogene, 2007, vol. 26, No. 25, pp. 3745-3757.
Supplementary European Search Report for corresponding European Application No. EP14878071.1 (dated May 10, 2017) (6 Pages).
Fujimori et al., 2002, The genus *Bifidobacterium* for cancer gene therapy, Curr.Opin.Drug.Disc.Develop.5(2),200-203.
Balkwill, "Tumour necrosis factor and cancer" |Nature Reviews, Cancer 9: 361-371.

(Continued)

*Primary Examiner* — Mindy G Brown
(74) *Attorney, Agent, or Firm* — Lucas & Mercanti, LLP

(57) ABSTRACT

An object of the present invention is to effectively induce cancer cell apoptosis using the anti-TRAIL-R1 antibody(ies) and the anti-TRAIL-R2 antibody(ies) and to reduce the toxicity imposed on normal cells. The present invention relates to recombinant obligate anaerobic Gram-positive bacteria that include a nucleic acid encoding a fusion protein having 3 or more anti-TRAIL-R1 single-chain antibodies and/or 3 or more anti-TRAIL-R2 single-chain antibodies, in an expressible state.

8 Claims, 28 Drawing Sheets
Specification includes a Sequence Listing.

(56) References Cited

OTHER PUBLICATIONS

Papadopoulos et al., 2015 "Unexpected hepatotoxicity in a phase I study of TAS266, a novel tetravalent agonistic Nanobody® targeting the DR5 receptor" Cancer Chemother Pharmacol 75:887-895.
Holland, 2014, "Death receptor agonist therapies for cancer, which is the right TRAIL?" Cytokine & Growth Factor Reviews 25:185-193.
Mori, et al., 2004 "Human normal hepatocytes are susceptible to apoptosis signal mediated by both TRAIL-R1 and TRAIL-R2" Cell Death and Differentiation 11: 203-207.
EPO Communication pursuant to Article 94(3) EPC (Office Action) dated Sep. 13, 2017.

* cited by examiner a b a b

SEQUENCE LISTING

```
<160> NUMBER OF SEQ ID NOS: 29

<210> SEQ ID NO 1
<211> LENGTH: 2064
<212> TYPE: DNA
<213> ORGANISM: Artificial
<220> FEATURE:
<223> OTHER INFORMATION: Synthetic

<400> SEQUENCE: 1
aagctttggg cgcggcggcc atgaagtggc ttgacaagca caatctcgtc tgattttgc      60 ccttgccctc ccctcgaaaa aaacacataa atcctatata aaatgcgggt tttcgcagtc    120
acatgcgcta ttatcattga ttgaacgggc aaagcaacaa atgccgcccc ctgaccaaga    180
aggatgcttt atgaccaatg tgcgcgtcat caagcctgca ctggccgccc tggttgccgc    240
cgccgcatgc gtgggcgggc tggcctttag cagcgcgcag ccggcccagg ctgacaccta    300
tgaagtccag ctggtagaga gcggaggcgg cagcgtacag gccggggaca gcctgagact    360
gtcctgcgcg gctagtggcc gtacctttgg ctccataagg gttgggtggt tccgccaaac    420
cccgggcaag gagcgtgagt ttgtcgcggc cataaaccgc aacgatggta cgacctatta    480
tgccgacagc gtcaagggcc ggttcaccat cagtcgtgac aacgctaaga acactgttta    540
catgcagatg gcatccctga agcccgagga taccgccgtg tactattgcg cagctgggct    600
gcaatacaac cgcagcgcgg accgcgtgcc tgtcggcgca gtatactggg gccaaggcac    660
ccaagtgacg gtgtccagtg gcggtagtgg cggaggcggc tcgggcggag aggtgcagct    720
cgtcgaaagt ggcggaggta gcgtgcaggc gggcgattcg ctgcgtttgt cgtgcgcggc    780
cagcggccgg acattcggtt ccatccgcgt cggttggttc cgccagactc cgggtaaaga    840
aagggagttc gtggccgcca tcaaccgtaa cgacggtacc acttactatg ccgactccgt    900
gaaagggcgc tttacaatct cgcgcgacaa cgcgaagaat acggtttaca tgcagatggc    960
```

```
aagcctcaaa ccggaggaca cggccgtata ctattgcgcc gcgggcctgc agtacaaccg     1020
gtccgccgac agggtgccgg tcggggccgt gtactggggt cagggtaccc aggtgactgt     1080
ctccagcggt ggaagtggag gtggtggcag cggtggggag gtccagctgg tggaatccgg     1140
cggcggatcc gtgcaagcgg gagatagtct gcgcttgtcg tgcgcagcgt ccggccgcac     1200
ctttggcagc attcgtgtgg gctggttcag gcagacccca ggcaagagc gggaattcgt      1260 ggccgctatc aaccgcaatg acggcacaac atattacgcc gattccgtca agggacggtt     1320
cacgatctcc cgcgacaatg cgaagaacac cgtgtatatg cagatggcgt cgcttaaacc     1380
ggaagatacc gccgtctact actgcgctgc cggccttcag tataaccgct ccgcagaccg     1440
tgtcccggtg ggcgccgtgt attggggtca aggcacccag gtcaccgtca gttcgggcgg     1500
ctccggagga ggcggctccg gaggcgaagt gcagctggtc gaatccggcg gtggttcggt     1560
gcaggccgga gactccctcc gcctgtcctg tgcggcgtcc ggacgtacct tcggatccat     1620
tcgcgtcgga tggtttcgtc agacaccggg caaggaaaga gagttcgtgg cggccattaa     1680
tcggaatgac ggaaccacgt attatgcaga ctcggttaag gggcgcttca ctatcagccg     1740
cgataacgcc aagaacacgg tctacatgca aatggcctcc ctcaaacccg aggatacggc     1800
cgtttattac tgtgcggctg gcttgcagta taacaggtcg gccgacagag tccccgtggg     1860
cgctgtctat tggggccagg gcacccaggt aacggtttcc tcccaccacc atcaccacca     1920
ttgaactagt ccttctgctc gtagcgatta cttcgagcat tactgacgac aaagaccccg     1980
accgagatgg tcgggtctt tttgttgtgg tgctgtgacg tgttgtccaa ccgtattatt      2040
ccggactaga tcagcggcgg ccgc                                            2064
```

<210> SEQ ID NO 2
<211> LENGTH: 2340
<212> TYPE: DNA
<213> ORGANISM: Artificial
<220> FEATURE:
<223> OTHER INFORMATION: Synthetic

<400> SEQUENCE: 2

```
aagctttggg cgcggcggcc atgaagtggc ttgacaagca caatctcgtc tgattttgc      60 ccttgccctc ccctcgaaaa aaacacataa atcctatata aaatgcgggt tttcgcagtc     120
acatgcgcta ttatcattga ttgaacgggc aaagcaacaa atgccgcccc ctgaccaaga    180
aggatgcttt atgaccaatg tgcgcgtcat caagcctgca ctggccgccc tggttgccgc    240
cgccgcatgc gtgggcgggc tggcctttag cagcgcgcag ccggcccagg ctgacaccta    300
tgaagtccag ctggtggaaa gcggaggagg ctccgtgcaa gctggagaca gcctgagact    360
gtcctgtgca gctccggta ggacctttgg ctcgattcgc gtcggatggt tccgtcagac     420
ccctggcaag gaacgtgagt tcgttgccgc catcaacagg aacgacggca ccacctatta    480
cgcggactcc gtcaaaggcc gcttcaccat ctcgagagac aacgccaaga acacggtcta    540
catgcagatg gccagcctga agccggagga cactgcggtc tactattgcg ctgccggggtt   600 gcagtataac cgcagtgccg atcgtgtgcc ggtaggggcc gtctattggg gccagggtac    660
ccaggtcacc gtgtcctccg gcggcagcgg aggcggcggg agcggcggtg aagtccagct    720
cgttgaaagc ggtggcggat ccgtgcaagc gggcgattcc ctgcggcttt cctgcgcagc    780
cagtggccgg acgttcggta gcatacgtgt cggctggttt cgccaaactc cgggcaaaga    840
gcgcgagttc gtagcggcga tcaaccgcaa tgacggcact acctactacg cagattcggt    900
```

| | |
|---|---|
| gaaagggcgc ttcacgattt cccgcgacaa tgccaagaat acggtgtata tgcagatggc | 960 |
| gtcgctcaag cccgaggata cggccgtgta ttactgcgcc gctggcctgc agtacaacag | 1020 |
| gagcgcagac cgggtaccag tgggcgcggt ttattgggt cagggcacac aggtgacagt | 1080 |
| gagttcctct agagagggag gcagcctggc tgctctgaca cgcaccagg cctgccatct | 1140 |
| gcccctggaa acgtttaccc ggcaccgcca gccgcgcggg tgggagcaac tggagcagtg | 1200 |
| cggctacccg gtccagaggc tggtcgctct gtatctcgcg gcccgtttgt cctggaatca | 1260 |
| ggtggatcag gtaattcgga acgccctggc aagccctggg tcgggaggcg atctgggcga | 1320 |
| agccataagg gaacagccgg aacaggccag gctggcccctt actctggcgg cggcggagtc | 1380 |
| cgagcgcttc gtccgtcagg gcaccgggaa cgacgaagct ggtgccgcga atgccgacgt | 1440 |
| ggtttccctc acatgcccgg tggcggcagg cgaatgcgcc gggccggccg actccggcga | 1500 |
| cgcgcttctg gaacgcaact atcccaccgg ggccgaattc ctgggtgatg gcggagatgt | 1560 |
| ttccttctcc acccgtggca cgcagaactg gacggtcgaa cggctgttgc aggcgcaccg | 1620 |
| ccagttggaa gagagaggtt atgtgttcgt tggctaccat gggacgttcc tggaagccgc | 1680 |
| ccaatccatc gtgttcggtg gcgttcgcgc gcgctcccag gatttggacg ccatctggag | 1740 |
| gggatttttat atagcgggtg acccggcctt ggcctatgga tacgcgcagg accaggagcc | 1800 |
| ggatgcgcgt gggcgcatac gtaacggcgc cctcctgcgc gtgtatgtgc ctaggagtag | 1860 |
| cttgcctggc ttctatcgca cgtccctgac gctggcggcc ccggaggcag caggcgaagt | 1920 |
| cgagcgtctg atcggccatc cgctgccact gagactggac gccatcaccg gaccggaaga | 1980 |
| ggagggcggc aggctcgaga ctatccttgg ctggcctctg gctgagcgca ctgtcgtgat | 2040 |
| tccatccgcg attcccaccg acccgcgtaa cgtgggcggc gatctcgatc cgtcgtcgat | 2100 |
| cccgacaag gaacaggcga tcagcgcgct tcccgactac gctagccagc ccggtaaacc | 2160 |
| gccccgcgag gacctgaagc accaccacca tcatcattga actagtcctt ctgctcgtag | 2220 |
| cgattacttc gagcattact gacgacaaag accccgaccg agatggtcgg ggtctttttg | 2280 |
| ttgtggtgct gtgacgtgtt gtccaaccgt attattccgg actagatcag cggcggccgc | 2340 |

<210> SEQ ID NO 3
<211> LENGTH: 2001
<212> TYPE: DNA
<213> ORGANISM: Artificial
<220> FEATURE:
<223> OTHER INFORMATION: Synthetic

<400> SEQUENCE: 3

| | |
|---|---|
| aagctttggg cgcggcggcc atgaagtggc ttgacaagca caatctcgtc tgattttttgc | 60 |
| ccttgccctc ccctcgaaaa aaacacataa atcctatata aaatgcgggt tttcgcagtc | 120 |
| acatgcgcta ttatcattga ttgaacgggc aaagcaacaa atgccgcccc ctgaccaaga | 180 |
| aggatgcttt atgaccaatg tgcgcgtcat caagcctgca ctggccgccc tggttgccgc | 240 |
| cgccgcatgc gtgggcgggc tggcctttag cagcgcgcag ccggcccagg ctgacaccta | 300 |
| tgaagtccag ctggtggaaa gcggaggagg ctccgtgcaa gctggagaca gcctgagact | 360 |
| gtcctgtgca gctccggta ggacctttgg ctcgattcgc gtcggatggt tccgtcagac | 420 |
| ccctggcaag gaacgtgagt tcgttgccgc catcaacagg aacgacggca ccacctatta | 480 |
| cgcggactcc gtcaaaggcc gcttcaccat ctcgagagac aacgccaaga acacggtcta | 540 |
| catgcagatg gccagcctga gccggagga cactgcggtc tactattgcg ctgccggggtt | 600 |
| gcagtataac cgcagtgccg atcgtgtgcc ggtaggggcc gtctattggg gccagggtac | 660 |

```
ccaggtcacc gtgtcctccg gcggcagcgg aggcggcggg agcggcggtg aagtccagct    720
cgttgaaagc ggtggcggat ccgtgcaagc gggcgattcc ctgcggcttt cctgcgcagc    780
cagtggccgg acgttcggta gcatacgtgt cggctggttt cgccaaactc cgggcaaaga    840
gcgcgagttc gtagcggcga tcaaccgcaa tgacggcact acctactacg cagattcggt    900
gaaagggcgc ttcacgattt cccgcgacaa tgccaagaat acggtgtata tgcagatggc    960
gtcgctcaag cccgaggata cggccgtgta ttactgcgcc gctggcctgc agtacaacag   1020
gagcgcagac cgggtaccag tgggcgcggt ttattgggt caggggcacac aggtgacagt   1080 gagttcctct agaggcggtt cgggcggagg tggctccggc ggtatggtgt ccaagggcga   1140
agagctgttc actggcgtgg tgccgatcct ggtggagctc gacggggacg tgaatggcca   1200
caaattcagc gtgtcgggcg aaggcgaagg cgacgccacc tacggcaagc tgacgctgaa   1260
attcatctgc accacgggca aactccccgt cccgtggccc accctggtca cgactctcac   1320
ctacggggtc cagtgcttct cccgttaccc tgaccacatg aagcaacacg acttcttcaa   1380
gtccgcgatg ccgagggct acgtgcagga acgcacgatc ttcttcaagg acgacggcaa   1440
ctacaagacc cgggccgagg tcaagttcga gggtgacacc cttgtgaatc gcatcgagct   1500
gaagggaatc gacttcaaag aggacggaaa cattctgggg cataagctcg agtacaacta   1560
caactcgcac aacgtgtaca tcatggctga caagcagaag aacggcatca aggtgaactt   1620
caagatccgc cataacatcg aggatggctc cgtccagctc gcggaccatt accagcagaa   1680 cacccccgatt ggcgatggtc ccgttctctt gccggacaac cactatctgt cgacgcagtc   1740
cgcgctgtcc aaggatccga acgagaagcg ggaccacatg gtgcttctcg agttcgtgac   1800
cgcagccggc atcaccctgg gaatggacga gctgtacaag caccaccatc accaccattg   1860
aactagtcct tctgctcgta gcgattactt cgagcattac tgacgacaaa gaccccgacc   1920
gagatggtcg gggtcttttt gttgtggtgc tgtgacgtgt tgtccaaccg tattattccg   1980
gactagatca gcggcggccg c                                             2001
```

<210> SEQ ID NO 4
<211> LENGTH: 1204
<212> TYPE: DNA
<213> ORGANISM: Artificial
<220> FEATURE:
<223> OTHER INFORMATION: Synthetic

<400> SEQUENCE: 4

```
ggtacccaac atgaagttat gcatattact ggccgtcgtg gcctttgttg gcctctcgct     60
cggggcaacc atcaaacttc atgatcaatc aattggcaca cagcaatggg aacatagccc    120
tttgggagag ttgtgtccac caggatctca tagatcagaa catcctggag cctgtaaccg    180
gtgcacagag ggtgtgggtt acaccaatgc ttccaacaat ttgtttgctt gcctcccatg    240
tacagcttgt aaatcagatg aagaagagag aagtccctgc accacgacca ggaacacagc    300
atgtcagtgc aaaccaggaa ctttccggaa tgacaattct gctgagatgt gccggaagtg    360
cagcagaggg tgccccagag ggatggtcaa ggtcaaggat tgtacgccct ggagtgacat    420
cgagtgtgtc cacaaagaat caggcaatgg acataatatt gaagggagaa tggatcccca    480
acctcaatcc caaccagaat gccggtgtcc caaatgtcca gcccctgagc tctgggagg    540 gccctcagtt ttcatcttcc ccccgaaacc caaggacgtc ctctccattt ctgggaggcc    600
cgaggtcacg tgcgttgtgg tagacgtggg ccaggaagac cccgaggtta gtttcaactg    660
```

```
gtacattgat ggcgctgagg tgcgaacggc caacacgaag ccaaagagg  aacagttcaa    720 cagcacgtac cgcgtggtca gcgtcctgcc catccggcac caggactggc tgacggggaa    780
ggaattcaag tgcaaggtca caacaaagc  tctcccagcc cccatcgaga ggaccatctc    840
caaggccaaa gggcagaccc gggagccgca ggtgtacgcc ctggcccac  accgggaaga    900 gctggccaag gacaccgtga gcgtaacatg cctggtaaaa gacttctacc cagttgacat    960
caacattgag tggcagagga acgggcagcc agagtcagag ggcacctacg ccaccacgcc   1020
gccacagctg gacaacgacg ggacctactt cctctacagc aagctctcgg tgggaaagaa   1080
cacgtggcag cggggagaaa ccttcacctg tgtggtgatg cacgaggccc tgcccaacca   1140
ctacacccag aaatctatca cccagtcttc gggtaaacat catcaccatc accattgact   1200
cgag                                                                1204
```

```
<210> SEQ ID NO 5
<211> LENGTH: 1198
<212> TYPE: DNA
<213> ORGANISM: Artificial
<220> FEATURE:
<223> OTHER INFORMATION: Synthetic

<400> SEQUENCE: 5
ggtacccaac atgaagttat gcatattact ggccgtcgtg gcctttgttg gcctctcgct     60
cggggctctg atcacccaac aagacctagc tccccagcag agagcggccc acaacaaaa    120 gaggtccagc ccctcagagg gattgtgtcc acctggacac catatctcag aagacggtag    180
agattgcatc tcctgcaaat atggacagga ctatagcact cactggaatg acctcctttt    240
ctgcttgcgc tgcaccaggt gtgattcagg tgaagtggag ctaagtccct gcaccacgac    300
cagaaacaca gtgtgtcagt gcgaagaagg caccttccgg gaagaagatt ctcctgagat    360
gtgccggaag tgccgcacag ggtgtcccag agggatggtc aaggtcggtg attgtacacc    420
ctggagtgac atcgaatgtg tccacaaaga aattgaaggg agaatggatc cccaaccctca   480 atcccaacca gaatgccggt gtcccaaatg tccagcccct gagctcctgg gagggccctc    540
agtcttcatc ttcccccga  aacccaagga cgtcctctcc atttctggga ggcccgaggt    600
cacgtgcgtt gtggtagacg tgggccagga agaccccgag gttagtttca actggtacat    660
tgatggcgct gaggtgcgaa cggccaacac gaagccaaaa  gaggaacagt tcaacagcac    720
gtaccgcgtg gtcagcgtcc tgcccatccg gcaccaggac tggctgacgg ggaaggaatt    780
caagtgcaag gtcaacaaca agctctccc  agccccatc  gagaggacca tctccaaggc    840 caaaggggcag acccgggagc cgcaggtgta cgccctggcc ccacaccggg aagagctggc    900
caaggacacc gtgagcgtaa catgcctggt aaaagacttc tacccagttg acatcaacat    960
tgagtggcag aggaacgggc agccagagtc agagggcacc tacgccacca cgccgccaca   1020
gctggacaac gacgggacct acttcctcta cagcaagctc tcggtgggaa agaacacgtg   1080
gcagcgggga gaaaccttca cctgtgtggt gatgcacgag gccctgccca accactacac   1140
ccagaaatct atcacccagt cttcgggtaa acatcatcac catcaccatt gactcgag    1198
```

```
<210> SEQ ID NO 6
<211> LENGTH: 1189
<212> TYPE: DNA
<213> ORGANISM: Artificial
<220> FEATURE:
<223> OTHER INFORMATION: Synthetic

<400> SEQUENCE: 6
```

```
ggtacccaac atgaagttat gcatattact ggccgtcgtg gcctttgttg gcctctcgct        60
cggggctaac ccagcccata atcgtccagc tggcctacac cggccggagg agagcccatc       120
aagaggaccc tgtctagcag gccagtacct gtcagaaggg aactgcaagc cttgcagaga       180
gggtattgac tacaccagcc attccaacca ttctctggat tcatgtattc tctgcacagt       240
ctgtaaggaa gataaagtcg tagaaacccg atgcaacata accacaaata cggtgtgtcg       300
atgcaaacca ggcacctttg aagataaaga ctccctgag atctgccagt catgctctaa        360
ctgcactgac ggggaagagg aactgacttc ctgtaccccc agagaaaacc ggaagtgtgt       420
ctccaaaacg gcttgggcat ctattgaagg gagaatggat ccccaacctc aatcccaacc       480
agaatgccgg tgtcccaaat gtccagcccc tgagctcctg ggagggccct cagtcttcat       540 cttcccccg aaacccaagg acgtcctctc catttctggg aggcccgagg tcacgtgcgt        600
tgtggtagac gtgggccagg aagaccccga ggttagtttc aactggtaca ttgatggcgc       660
tgaggtgcga acggccaaca cgaagccaaa agaggaacag ttcaacagca cgtaccgcgt       720
ggtcagcgtc ctgcccatcc ggcaccagga ctggctgacg gggaaggaat tcaagtgcaa       780
ggtcaacaac aaagctctcc cagcccccat cgagaggacc atctccaagg ccaaagggca       840
gacccgggag ccgcaggtgt acgccctggc cccacaccgg gaagagctgg ccaaggacac       900
cgtgagcgta acatgcctgg taaaagactt ctacccagtt gacatcaaca ttgagtggca       960
gaggaacggg cagccagagt cagagggcac ctacgccacc acgccgccac agctggacaa      1020
cgacgggacc tacttcctct acagcaagct ctcggtggga aagaacacgt ggcagcgggg      1080
agaaaccttc acctgtgtgg tgatgcacga ggccctgccc aaccactaca cccagaaatc      1140
tatcacccag tcttcgggta acatcatca ccatcaccat tgactcgag                   1189

<210> SEQ ID NO 7
<211> LENGTH: 440
<212> TYPE: DNA
<213> ORGANISM: Artificial
<220> FEATURE:
<223> OTHER INFORMATION: Synthetic

<400> SEQUENCE: 7
catatggagg tccagttagt agaatccggc ggtggctcag tacaagcggg cgattcactg        60
cgcctgagct gtgcggcgtc cggccgtacc tttggctcta tccgcgtagg ttggtttcgc       120
cagacgccgg gcaaagaacg cgaatttgtg gctgcgatta accgcaatga tgggaccacg       180
tactatgcgg actccgtcaa aggtcgcttc acgatttctc gcgataacgc caaaaatacg       240
gtgtatatgc agatggcatc cctgaaacca gaagataccg ccgtgtacta ttgtgcggca       300
ggtctgcagt ataatcgctc cgccgaccgc gttccagtag gtgccgtcta ctggggtcag       360
ggtacccagg taaccgttag ttcgaagctt gaacaaaaac tcatctcaga agaggatctg       420
aatggggccg cagcggccgc                                                  440

<210> SEQ ID NO 8
<211> LENGTH: 49
<212> TYPE: DNA
<213> ORGANISM: Artificial
<220> FEATURE:
<223> OTHER INFORMATION: Primer

<400> SEQUENCE: 8
ggtaaaggcc cagccggcca tggccgaggt gcagctcgtg gagtctggg                    49
```

<210> SEQ ID NO 9
<211> LENGTH: 41
<212> TYPE: DNA
<213> ORGANISM: Artificial
<220> FEATURE:
<223> OTHER INFORMATION: Primer

<400> SEQUENCE: 9
ttgcaagcaa ttgcggccgc tgaggagacg gtgacctggg t                41

<210> SEQ ID NO 10
<211> LENGTH: 56
<212> TYPE: DNA
<213> ORGANISM: Artificial
<220> FEATURE:
<223> OTHER INFORMATION: Primer

<400> SEQUENCE: 10
cccatatgtg gtcccatccg cagtttgaaa aagacaccta tgaagtccag ctggta        56

<210> SEQ ID NO 11
<211> LENGTH: 36
<212> TYPE: DNA
<213> ORGANISM: Artificial
<220> FEATURE:
<223> OTHER INFORMATION: Primer

<400> SEQUENCE: 11
aattgcggcc gctcaatggt ggtgatggtg gtggga                36

<210> SEQ ID NO 12
<211> LENGTH: 56
<212> TYPE: DNA
<213> ORGANISM: Artificial
<220> FEATURE:
<223> OTHER INFORMATION: Primer

<400> SEQUENCE: 12
cccatatgtg gtcccatccg cagtttgaaa aagacaccta tgaagtccag ctggtg        56

<210> SEQ ID NO 13
<211> LENGTH: 36
<212> TYPE: DNA
<213> ORGANISM: Artificial
<220> FEATURE:
<223> OTHER INFORMATION: Primer

<400> SEQUENCE: 13
aattgcggcc gccttcaggt cctggcgggg cggttt                36

<210> SEQ ID NO 14
<211> LENGTH: 44
<212> TYPE: DNA
<213> ORGANISM: Artificial
<220> FEATURE:
<223> OTHER INFORMATION: Primer

<400> SEQUENCE: 14
ttgcaagcaa ttgcggccgc cttgtacagc tcgtccattc ccag                44

<210> SEQ ID NO 15
<211> LENGTH: 5
<212> TYPE: PRT
<213> ORGANISM: Artificial
<220> FEATURE:
<223> OTHER INFORMATION: Recombinant construct -continued

<400> SEQUENCE: 15

Ser Ile Arg Val Gly
1               5

<210> SEQ ID NO 16
<211> LENGTH: 17
<212> TYPE: PRT
<213> ORGANISM: Artificial
<220> FEATURE:
<223> OTHER INFORMATION: Recombinant construct

<400> SEQUENCE: 16

Ala Ile Asn Arg Asn Asp Gly Thr Thr Tyr Tyr Ala Asp Ser Val Lys
1               5                   10                  15

Gly

<210> SEQ ID NO 17
<211> LENGTH: 17
<212> TYPE: PRT
<213> ORGANISM: Artificial
<220> FEATURE:
<223> OTHER INFORMATION: Recombinant construct

<400> SEQUENCE: 17

Gly Leu Gln Tyr Asn Arg Ser Ala Asp Arg Val Pro Val Gly Ala Val
1               5                   10                  15

Tyr

<210> SEQ ID NO 18
<211> LENGTH: 30
<212> TYPE: PRT
<213> ORGANISM: Artificial
<220> FEATURE:
<223> OTHER INFORMATION: Recombinant construct

<400> SEQUENCE: 18

Gln Gly Ile Lys Ala Arg Ser Gln Phe Val Glu Ser Gly Gly Gly Leu
1               5                   10                  15

Val Gln Pro Gly Gly Ser Leu Arg Leu Ser Cys Thr Ala Ser
            20                  25                  30

<210> SEQ ID NO 19
<211> LENGTH: 17
<212> TYPE: PRT
<213> ORGANISM: Artificial
<220> FEATURE:
<223> OTHER INFORMATION: Recombinant construct

<400> SEQUENCE: 19

Val Gly Trp Phe Arg Gln Ala Pro Gly Lys Glu Arg Glu Gly Val Leu
1               5                   10                  15

Cys

<210> SEQ ID NO 20
<211> LENGTH: 38
<212> TYPE: PRT
<213> ORGANISM: Artificial
<220> FEATURE:
<223> OTHER INFORMATION: Recombinant construct

<400> SEQUENCE: 20

Asn Val Ala Asn Ser Val Lys Gly Arg Phe Thr Ile Ser Arg Asp Asn
1               5                   10                  15

Asp Lys Asn Thr Val Tyr Leu Gln Met Asn Ser Leu Lys Pro Glu Asp
            20                  25                  30

Thr Ser Val Tyr Tyr Cys
        35

<210> SEQ ID NO 21
<211> LENGTH: 11
<212> TYPE: PRT
<213> ORGANISM: Artificial
<220> FEATURE:
<223> OTHER INFORMATION: Recombinant construct

<400> SEQUENCE: 21

Trp Gly Gln Gly Thr Gln Val Thr Val Ser Ser
1               5                   10

<210> SEQ ID NO 22
<211> LENGTH: 8
<212> TYPE: PRT
<213> ORGANISM: Artificial
<220> FEATURE:
<223> OTHER INFORMATION: Recombinant construct

<400> SEQUENCE: 22

Gly Arg Thr Phe Ser Ser Asn Val
1               5

<210> SEQ ID NO 23
<211> LENGTH: 8
<212> TYPE: PRT
<213> ORGANISM: Artificial
<220> FEATURE:
<223> OTHER INFORMATION: Recombinant construct

<400> SEQUENCE: 23

Ile Arg Trp Arg Gly Asp Ser Thr
1               5

<210> SEQ ID NO 24
<211> LENGTH: 10
<212> TYPE: PRT
<213> ORGANISM: Artificial
<220> FEATURE:
<223> OTHER INFORMATION: Recombinant construct

<400> SEQUENCE: 24

Ala Ala Ser Ser Gly Asn Thr Tyr Leu Tyr
1               5                   10

<210> SEQ ID NO 25
<211> LENGTH: 184
<212> TYPE: DNA
<213> ORGANISM: Artificial
<220> FEATURE:
<223> OTHER INFORMATION: Synthetic DNA derived from hup promoter of
      Bifidobacterium longum

<400> SEQUENCE: 25
tgggcgcggc ggccatgaag tggcttgaca agcacaatct cgtctgattt ttgcccttgc      60
cctcccctcg aaaaaaacac ataaatccta tataaaatgc gggttttcgc agtcacatgc     120
gctattatca ttgattgaac gggcaaagca acaaatgccg cccctgacc aagaaggatg     180 cttt                                                                  184

```
<210> SEQ ID NO 26
<211> LENGTH: 126
<212> TYPE: DNA
<213> ORGANISM: Artificial
<220> FEATURE:
<223> OTHER INFORMATION: Synthetic DNA derived from HUT terminator

<400> SEQUENCE: 26
ccttctgctc gtagcgatta cttcgagcat tactgacgac aaagaccccg accgagatgg      60
tcggggtctt tttgttgtgg tgctgtgacg tgttgtccaa ccgtattatt ccggactaga     120
tcagcg                                                                126

<210> SEQ ID NO 27
<211> LENGTH: 6
<212> TYPE: PRT
<213> ORGANISM: Artificial
<220> FEATURE:
<223> OTHER INFORMATION: Synthetic

<400> SEQUENCE: 27

Ile Glu Gly Arg Met Asp
1               5

<210> SEQ ID NO 28
<211> LENGTH: 10
<212> TYPE: PRT
<213> ORGANISM: Artificial
<220> FEATURE:
<223> OTHER INFORMATION: Synthetic

<400> SEQUENCE: 28

Gly Gly Ser Gly Gly Gly Gly Ser Gly Gly
1               5                   10

<210> SEQ ID NO 29
<211> LENGTH: 102
<212> TYPE: DNA
<213> ORGANISM: Artificial
<220> FEATURE:
<223> OTHER INFORMATION: Synthetic DNA derived from usp secretory signal
      sequence of Bifidobacterium longum

<400> SEQUENCE: 29
atgaccaatg tgcgcgtcat caagcctgca ctggccgccc tggttgccgc cgccgcatgc      60
gtgggcgggc tggcctttag cagcgcgcag ccggcccagg ct                        102
```

RECOMBINANT OBLIGATE ANAEROBIC GRAM-POSITIVE BACTERIA

CROSS-REFERENCE TO RELATED APPLICATIONS

This application is a 371 of PCT/JP2014/084038, filed Dec. 24, 2014, which claims the benefit of Japanese Patent Application No. 2014-003441, filed Jan. 10, 2014.

TECHNICAL FIELD

The present invention relates to an antitumor agent and a marker for tumor detection comprising recombinant obligate anaerobic Gram-positive bacteria as an active ingredient.

BACKGROUND ART

A TNF-related apoptosis-inducing ligand (TRAIL) belongs to the TNF superfamily, and is a protein that induces apoptosis in various types of cancer cells. TRAIL forms a trimer in vivo and binds to a TRAIL receptor (e.g., TRAIL-R1 or TRAIL-R2) containing a death domain in its intracellular region. When TRAIL binds to TRAIL receptors, they aggregate with each other to form a trimer, and apoptotic signals are then transmitted intracellularly. Examples of known TRAIL receptors include TRAIL-R3, TRAIL-R4, and a soluble receptor (i.e., osteoprotegerin), in addition to the TRAIL-R1 and TRAIL-R2 described above (FIG. 1). TRAIL-R3, TRAIL-R4, and osteoprotegerin completely or partially lack death domains, and such receptors do not induce apoptosis even if TRAIL binds thereto. Thus, such receptors are referred to as "decoy receptors."

TRAIL is less likely to cause apoptosis of normal cells. Thus, the development thereof as an antitumor agent has been in progress. In order to efficiently induce cancer cell apoptosis with the use of TRAIL, however, it is necessary to develop a system in which TRAIL efficiently binds to TRAIL-R1 and TRAIL-R2 without binding to the decoy receptors to deliver apoptotic signals to the cells. Agonistic antibodies against TRAIL-R1 and TRAIL-R2 can induce apoptosis more effectively than TRAIL, since they do not bind to the decoy receptors, and administration intervals of such antibodies may be longer, since the blood half-life thereof is longer. Accordingly, such antibodies have been subjected to clinical trials (Non-Patent Document 1). However, since HGS-ETR1 (anti-hTRAIL (human TRAIL)-R1 agonistic antibody) and HGS-ETR2 (anti-hTRAIL-R2 agonistic antibody) are divalent antibodies, these antibodies cannot induce trimer formation of TRAIL receptors, without cross-linking of antibodies by NK cells or macrophages having Fc receptors (FIG. 2a). Thus, remarkable therapeutic effects could not be attained through clinical trials of these antibodies (Non-Patent Document 2).

HGS-TR2J (KMTR2) is known as a potent agonistic antibody that allows hTRAIL-R2 molecules on cancer cell membranes to directly aggregate and deliver apoptotic signals without the aid of NK cells or macrophages (Non-Patent Document 3) (FIG. 2b). It is also known that a trimer, tetramer, or pentamer of the llama-derived single-chain VHH antibody against hTRAIL-R2 would very strongly induce apoptosis of cancer cells expressing hTRAIL-R2 without the aid of NK cells or macrophages (Patent Document 1) (FIG. 3). In contrast, hTRAIL-R1 and hTRAIL-R2 are expressed in various normal human tissues as well as cancer cells. In particular, normal human hepatic cells are sensitive to hTRAIL and the hTRAIL-R agonistic antibody (Non-Patent Document 4 and Non-Patent Document 5). Thus, the hTRAIL-R agonistic antibody is considered to cause hepatic disorders as side effects.

PRIOR ART DOCUMENTS

Patent Documents

Patent Document 1: PCT WO/2011/098520

Non-Patent Documents

Non-Patent Document 1: Ghobrial et al., 2005, CA. Cancer J. Clin., 55 (3), pp. 178-194
Non-Patent Document 2: Micheau et al., 2013, Br. J. Pharmacol., 169 (8), pp. 1723-1744
Non-Patent Document 3: Motoki et al., 2005, Clin. Cancer Res., 11 (8), pp. 3126-3135
Non-Patent Document 4: Jo et al., 2000, Nat. Med., 6 (5), pp. 564-567
Non-Patent Document 5: Mori et al., 2004, Cell Death Differ., 11 (2), pp. 203-207

SUMMARY OF THE INVENTION

Problem to be Solved by the Invention

It is an object of the present invention to induce effective cancer cell apoptosis using the anti-TRAIL-R1 antibody(ies) or the anti-TRAIL-R2 antibody(ies), and to reduce the toxicity imposed on normal cells.

Means for Solving Problem

The present inventors have conducted concentrated studies in order to solve the above problem. As a result, the present inventors prepared a recombinant *Bifidobacterium* strain expressing and secreting anti-hTRAIL-R2 VHH antibody(ies) having potent agonistic activity, and discovered that intravenous administration of the *Bifidobacterium* strain induced cancer cell apoptosis at tumor foci. In addition, the present inventors obtained a novel anti-hTRAIL-R1 VHH antibody capable of recognizing hTRAIL-R1 molecules on the cancer cell membrane. According to the present invention, cancer cell apoptosis can be effectively induced while reducing the toxicity imposed on normal cells via topical administration of the anti-hTRAIL-R1 antibody or the anti-hTRAIL-R2 antibody having potent agonistic activity.

The present invention is based on the results of the studies described above, and provides the following embodiments.

(1) Recombinant obligate anaerobic Gram-positive bacteria comprising a nucleic acid encoding a fusion protein comprising a signal peptide and 3 or more anti-TRAIL-R1 single-chain antibodies and/or 3 or more anti-TRAIL-R2 single-chain antibodies, in an expressible state.

(2) The recombinant obligate anaerobic Gram-positive bacteria of (1), wherein the obligate anaerobic Gram-positive bacteria belong to the genus *Bifidobacterium*.

(3) The recombinant obligate anaerobic Gram-positive bacteria of (1) or (2), wherein the anti-TRAIL-R1 single-chain antibody comprises CDR1 comprising the amino acid sequence as shown in SEQ ID NO: 22, CDR2 comprising the amino acid sequence as shown in SEQ ID NO: 23, and CDR3 comprising the amino acid sequence as shown in SEQ ID NO: 24.

(4) The recombinant obligate anaerobic Gram-positive bacteria of any of (1) to (3), wherein the anti-TRAIL-R2 single-chain antibody comprises CDR1 comprising the amino acid sequence as shown in SEQ ID NO: 15, CDR2 comprising the amino acid sequence as shown in SEQ ID NO: 16, and CDR3 comprising the amino acid sequence as shown in SEQ ID NO: 17.

(5) The recombinant obligate anaerobic Gram-positive bacteria of any of (1) to (4), wherein the fusion protein further comprises one or more functional peptides.

(6) The recombinant obligate anaerobic Gram-positive bacteria of (5), wherein the functional peptides comprises a labeling protein.

(7) An antitumor agent comprising, as an active ingredient, the recombinant obligate anaerobic Gram-positive bacteria of any of (1) to (6).

(8) An anti-TRAIL-R1 antibody comprising CDR1 comprising the amino acid sequence as shown in SEQ ID NO: 22, CDR2 comprising the amino acid sequence as shown in SEQ ID NO: 23; and CDR3 comprising the amino acid sequence as shown in SEQ ID NO: 24.

This description includes all or part of the contents disclosed in the description and/or drawings of Japanese Patent Application No. 2014-003441, to which the present application claims priority.

According to the present invention, cancer cell apoptosis can be effectively induced while reducing the toxicity imposed on normal cells via topical administration of the anti-hTRAIL-R1 antibody(ies) and the anti-hTRAIL-R2 antibody(ies) having potent agonistic activity to tumor foci.

MODES FOR CARRYING OUT THE INVENTION

Figure 1:
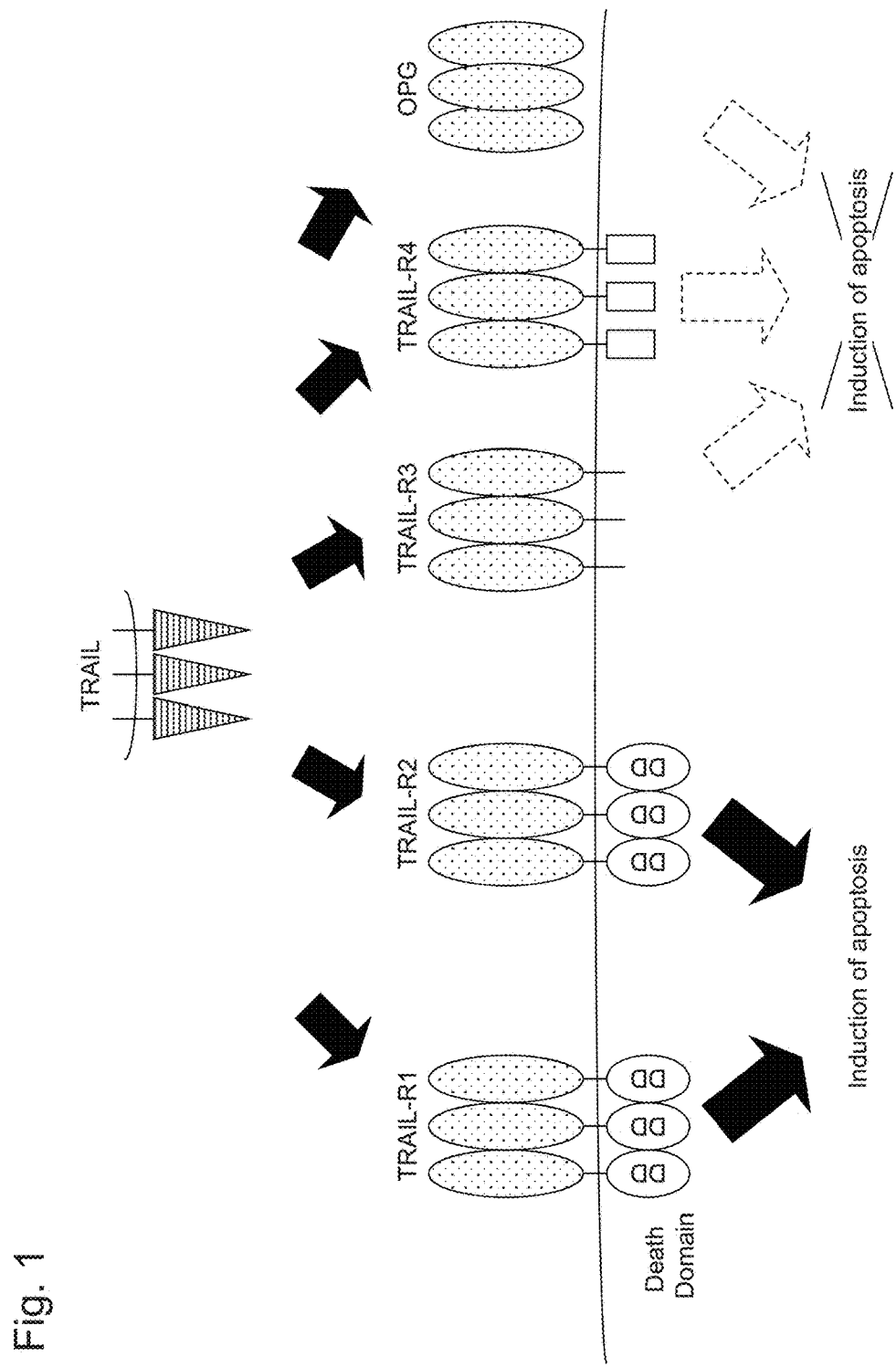
FIG. 1 schematically shows the structures of TRAIL and receptors thereof and signal transmission for apoptosis induction.
Figure 2:
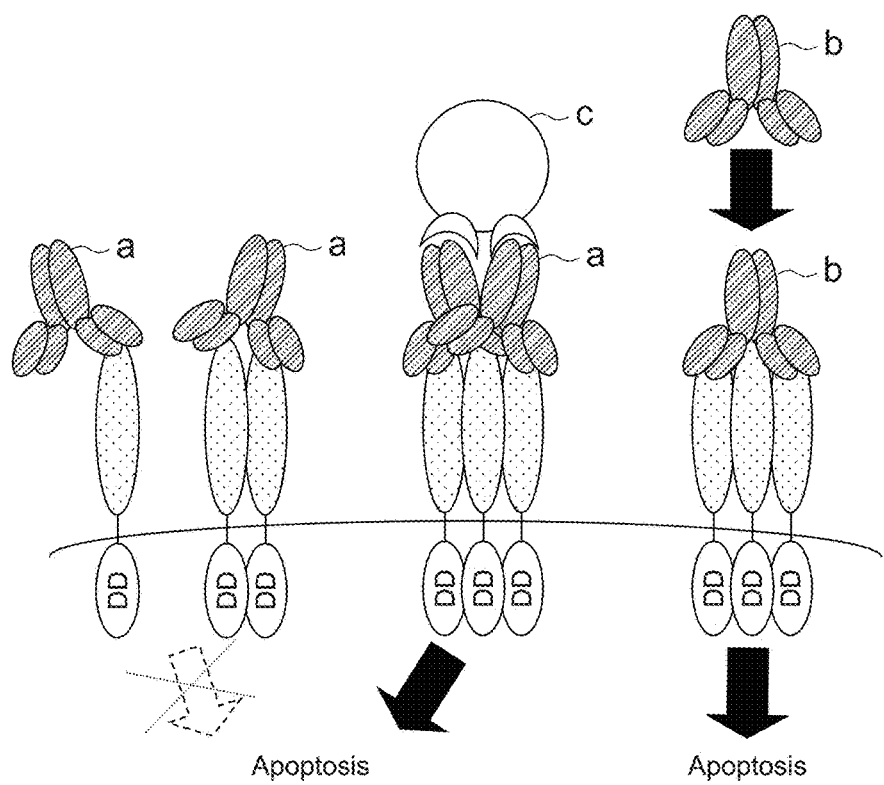
FIG. 2 schematically shows differences in terms of intracellular transmission of apoptotic signals between a general antibody "a" against TRAIL-R and an antibody "b" having agonistic activity. (In the case of a general antibody, crosslinking by NK cells or macrophages "c" is required for TRAIL-mediated apoptosis. In the case of the KMTR2 antibody, crosslinking by NK cells or macrophages is not required for TRAIL-mediated apoptosis.)
Figure 3:
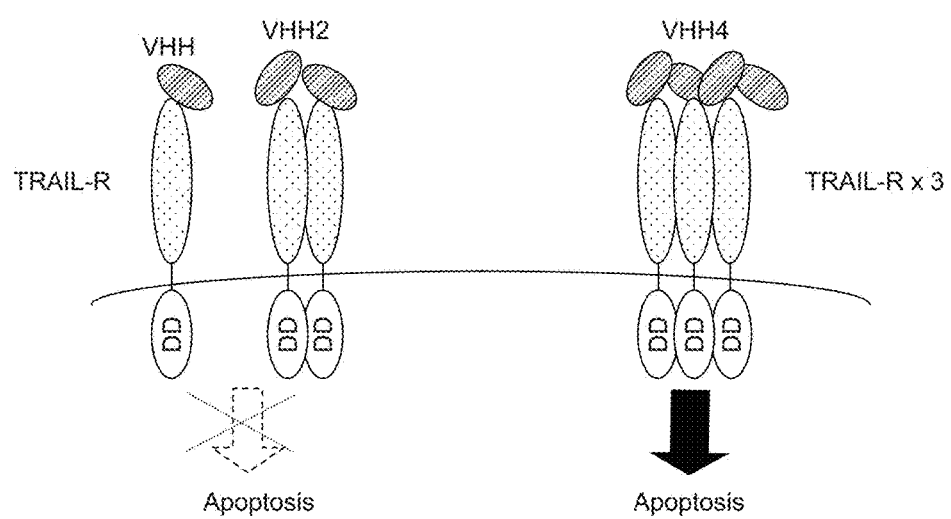
FIG. 3 schematically shows that a trimer, tetramer, or pentamer of the single-chain VHH antibody (VHH4 in FIG. 3) induces apoptosis of cancer cells expressing hTRAIL-R without crosslinking by NK cells or macrophages.

The present invention will be described below in detail.

1. Recombinant Obligate Anaerobic Gram-Positive Bacterium

1-1. Overview and Definition

A first aspect of the present invention is a recombinant obligate anaerobic gram-positive bacterium (hereinafter, often abbreviated as "recombinant bacteria (or bacterium)"). The recombinant bacterium of the present invention is a drug delivery carrier containing a nucleic acid encoding a fusion protein in an expressible state.

The term "obligate anaerobic Gram-positive bacteria (or bacterium)" refers to obligate anaerobes that are classified as Gram-positive bacteria. Herein, the term "obligate anaerobes" refers to bacteria that are also referred to as "strictly/obligately anaerobic bacteria" that cannot grow and die at high oxygen concentrations. In a mammalian body, therefore, these bacteria can grow in a low-oxygen anaerobic state, such as within digestive organs and mainly in the intestine, but they cannot grow in body fluids such as blood in which dissolved oxygen is present, or in general tissues. The term "Gram-positive bacteria (or bacterium)" refers to the generic name of bacteria that are stained violet or dark blue by Gram staining. Gram-positive bacteria include, but not limited to, bacilli, cocci, and spirilli herein. Since Gram-positive bacteria do not contain endotoxins, they do not release endotoxins after their death. Therefore, Gram-positive bacteria are preferable as drug delivery carriers of the present invention in terms of safety. Examples of the recombinant bacteria of the present invention include those of the genus *Bifidobacterium* (hereinafter "those of the genus *Bifidobacterium*" are referred to collectively as "*Bifidobacterium*" as a generic name) and those of the genus *Clostridium*. A preferable example thereof is *Bifidobacterium*. This is because *Bifidobacterium* does not secrete exotoxin, it is in daily use as a lactic acid bacterium, and it has been confirmed to be safe, for example, for human bodies. *Bifidobacterium* may be of any species. Preferable examples thereof are species that inhabit the human intestine, in particular, *B. bifidum, B. longum, B. brave, B. infantis*, and *B. adolescentis*.

1-2. Configuration

The obligate anaerobic gram-positive bacterium of the present invention contains a nucleic acid encoding a fusion protein (hereinafter, often referred to as "fusion gene") in an expressible state. Hereinafter, the fusion gene, by which the recombinant bacterium of the present invention is characterized, and the configuration of an expression cassette that enables the expression of the fusion gene are specifically described.

1-2-1. Configuration of Fusion Gene

The term "nucleic acid encoding a fusion protein" (or "fusion gene") as used herein refers to a foreign nucleic acid encoding a fusion protein that is constructed by the fusion of a plurality of genes, etc., using gene-recombination technology. The fusion gene is inserted into an expression cassette described later which is introduced into the recombinant bacteria of the present invention.

The term "fusion protein" as used herein refers to an extracellular secretory protein containing signal peptide(s), 3 or more single-chain antibodies, and, optionally, one or more functional peptides, which are linked. The signal peptide(s), the single-chain antibodies, and the functional peptides may be directly linked or indirectly linked via linker peptides. The length and the amino acid sequence of a linker peptide are not particularly limited, as long as it does not inhibit the functions of the single-chain antibodies and the functional peptides. A preferred example of the linker is an amino acid sequence that has a length of 20 amino acids or less or 15 amino acids or less and is not self-folded. Examples of linker peptides that can be used in the present invention include the IEGRMD linker peptide (SEQ ID NO: 27) and the (GGSGG)$_2$ linker peptide (SEQ ID NO: 28). Hereinafter, such a signal peptide, single-chain antibodies, and functional peptides that compose a fusion protein are specifically described.

(1) Signal Peptide

A signal peptide is required for the extracellular transfer of a protein that is biosynthesized within cells. In general, the signal peptide comprises positively charged amino acids such as Lys and Arg on the N-terminal side followed by highly hydrophobic amino acids such as Ala, Leu, Val, Ile, Val, and Phe. Moreover, the signal peptide may contain, on the C-terminal side thereof, an insertion sequence (following the signal sequence), which facilitates the cleavage of the signal peptide and secretion and/or an amino acid sequence comprising a site recognized by a signal peptidase cleaving the signal peptide from the fusion protein. The signal peptide plays a role in extracellularly secreting the fusion protein that is expressed within the bacteria of the present invention via a translocator or the like that exists on the membrane. The amino acid sequence of the signal peptide is not particularly limited. The amino acid sequences of any known signal sequences capable of functioning within obligate anaerobic Gram-positive bacteria can be used herein. Also, the amino acid length of a signal peptide is not particularly limited. In general, the length may range from 3 to 60 amino acids. A signal peptide with a short amino acid length is preferable, because, in such case, the molecular weight of the fusion protein is not too large.

The signal peptide is positioned on the N-terminal side of the fusion protein.

(2) Single-chain Antibody

The above fusion protein contains 3 or more single-chain antibodies. The term "single-chain antibody" as used herein refers to an antibody that is composed of a single-chain polypeptide, and is able to recognize and bind to a target substance alone. An antibody composed of two or more chains is too large in terms of molecular weight, and thus such an antibody is unlikely to be expressed and an appropriate three dimensional structure having antibody functions is unlikely to be constructed within obligate anaerobic Gram-positive bacteria. Therefore, the single-chain antibody of the present invention is preferably a low-molecular-weight antibody having a molecular weight of 35 kDa or less per molecule. The single-chain antibody may be either a natural antibody or an artificial antibody.

The single-chain antibody according to the present invention is typically comprises a variable region consisting of a complementarity determining region (CDR) and a framework region (FR). A complementarity determining region is a variable region that imparts binding specificity to an antibody. In contrast, a framework region is a relatively conserved region within a variable region. A complete variable domain comprises 4 FRs linked with 3 CDRs. Three CDRs are referred to as CDR1, CDR2, and CDR3 in order from the N terminus, and 4 FRs are referred to as FR1, FR2, FR3, and FR4 in order from the N terminus. In a variable region, accordingly, CDRs and FRs are positioned in the order of FR1, CDR1, FR2, CDR2, FR3, CDR3, and FR4 from the amino acid terminus toward the carboxy terminus.

The term "natural antibody" as used herein refers to an antibody having the same amino acid sequence as that of an antibody that is produced by any vertebrate. A specific example of a natural single-chain antibody is a single-chain antibody that is produced by animals of the family Camelidae (Hamers-Casterman C., et al., 1993, Nature, 363: 446-448) (hereinafter, referred to as a "single-chain antibody of the family Camelidae"). The single-chain antibody of the family Camelidae is composed of an H chain alone (without an L chain), it is able to bind to an antigen through the $V_H$ region of its H chain alone, and the molecular weight thereof is thus about 14 kDa, which is only about one-tenth the molecular weight of a general antibody. Moreover, the single-chain antibody of the family Camelidae generally has high antigen affinity, and it is characterized by high resistance to heat, acid, and base (Deffar, K., et al., 2009, African Journal of Biotechnology 8 (12): 2645-2652). Therefore, a single-chain antibody of the family Camelidae is very preferable as a single-chain antibody in the present invention. Any animal species of the family Camelidae can be used herein, as long as it can produce a single-chain antibody of the family Camelidae. For example, antibodies from any animal species such as lamas, alpacas, and camels can be used.

The term "artificial antibody" as used herein refers to an artificially constructed antibody. Examples thereof include a single-chain antibody prepared by introducing appropriate mutation(s) into the amino acid sequence of the aforementioned natural antibody as well as a structurally modified single-chain antibody that does not exist in principle in nature. Specific examples of such artificial antibody include a chimeric antibody, a humanized antibody, a single-chain Fv (scFv: a single-chain fragment of a variable region) (Pierce Catalog and Handbook, 1994-1995, Pierce Chemical Co., Rockford, Ill.), a diabody, a triabody, and a tetrabody.

A "chimeric antibody" refers to an antibody whose variable region and constant region are derived from different animal species. A chimeric antibody can be produced in accordance with a conventional technique, for example, by linking a nucleic acid encoding an antibody V region with a nucleic acid encoding a human antibody C region, incorporating the resultant into an expression vector, and introducing the expression vector into a host.

A "humanized antibody" is a modified antibody also referred to as a reshaped human antibody. A humanized antibody is constructed by grafting CDRs of an antibody derived from an immunized animal onto a complementarity determining region of a human antibody. A general gene recombination technique therefor is also known.

A single-chain Fv is a synthetic antibody having a molecular weight of about 35 kDa or less and a structure in which a polypeptide chain contains variable regions in the L and H chains of an immunoglobulin molecule (that is, $V_L$ and $V_H$, respectively), which are linked via a flexible linker with a sufficient length. Both variable regions can self-assemble to form a functional antigen binding site in a single-chain Fv.

The above fusion protein needs to comprise 3 or more single-chain antibodies, so as to allow TRAIL-R to aggregate and form a trimer. As the number of antibodies increases, however, the molecular weight of the fusion protein becomes larger. In general, accordingly, the number of single-chain antibodies is preferably several, such as 3 to 6, 3 to 5, or 3 or 4. Individual single-chain antibodies are desirably linked via appropriate linker peptide(s). The length and the amino acid sequence of a linker peptide are not particularly limited, as long as it does not inhibit the antigen binding activity of each single-chain antibody.

The above fusion protein comprises 3 or more single-chain antibodies that recognize the same antigen. When hTRAIL-R1 is an antigen, for example, the fusion protein comprises 3 or more single-chain antibodies that recognize the same hTRAIL-R1.

In the present invention, the term "valency" of the antibody refers to the number of antigen-binding sites of a single antibody molecule. For example, IgG is a divalent antibody having two antigen-binding sites in a single molecule. The single-chain antibody is a monovalent antibody having one antigen-binding site in a single molecule. Since the fusion protein of the present invention comprises 3 or more single-chain antibodies, the fusion protein is tri- or more valent as a whole.

The order of single-chain antibodies and functional peptide(s) described later is not particularly limited, as long as the antibodies are positioned on the C-terminal side of a signal peptide in a fusion protein. Single-chain antibodies are preferably positioned on the N-terminal side of functional peptide(s).

In the present invention, a target substance of a single-chain antibody is TRAIL-R1 or TRAIL-R2. As described above, the recombinant bacteria of the present invention can grow only in anaerobic environments. Accordingly, cells in an anaerobic environment in vivo are preferable target cells. Specifically, preferable examples thereof include tumor cells and intestinal epithelial cells. Hereafter, the anti-TRAIL-R1 antibody and the anti-TRAIL-R2 antibody are described in detail.

(i) Anti-TRAIL-R1 Antibody

In the present invention, the term "anti-TRAIL-R1 single-chain antibody" refers to a single-chain antibody against TRAIL-R1 (TNF-related apoptosis-inducing ligand receptor 1; TRAIL receptor 1). The anti-TRAIL-R1 single-chain antibody used in the present invention is not particularly limited, provided that it can specifically bind to TRAIL-R1. An example of an anti-TRAIL-R1 single-chain antibody that can be used in the present invention is 4P6, which was obtained and used in the examples of the present specification. 4P6 is a single-chain VHH antibody derived from alpaca, and comprises CDR1 comprising the amino acid sequence as shown in SEQ ID NO: 22, CDR2 comprising the amino acid sequence as shown in SEQ ID NO: 23, and CDR3 comprising the amino acid sequence as shown in SEQ ID NO: 24. The sequence of the framework region of the anti-TRAIL-R1 single-chain antibody used in the present invention is not particularly limited. For example, the sequence of a framework region of the alpaca-derived single-chain antibody described in Maass D. R., et al., 2007, J. Immunol. Methods, 324: 13-25 (e.g., Clone A02 described therein) can be used. Accordingly, the anti-TRAIL-R1 single-chain antibody may comprise for example, FR1 comprising the amino acid sequence as shown in SEQ ID NO: 18, FR2 comprising the amino acid sequence as shown in SEQ ID NO: 19, FR3 comprising the amino acid sequence as shown in SEQ ID NO: 20, and FR4 comprising the amino acid sequence as shown in SEQ ID NO: 21, although the constitution is not limited thereto.

It is particularly preferable that the fusion protein used in the present invention have agonistic activity of binding to TRAIL-R1 and inducing apoptosis. TRAIL-R1 induces apoptosis upon aggregation to form trimer or larger multimer. In order to activate TRAIL-R1, accordingly, it is particularly preferable that the fusion protein comprise 3 or more, 4 or more, 5 or more, or 6 or more, for example, 3, 4, 5, or 6 anti-TRAIL-R1 single-chain antibodies, as described above.

One aspect of the present invention relates to the anti-TRAIL-R1 antibody comprising CDR1 comprising the amino acid sequence as shown in SEQ ID NO: 22, CDR2 comprising the amino acid sequence as shown in SEQ ID NO: 23, and CDR3 comprising the amino acid sequence as shown in SEQ ID NO: 24. The sequence of the framework region of the antibody is not particularly limited. For example, the sequence described in the literature of Maass D. R. may be employed. That is, the antibody may comprise FR1 comprising the amino acid sequence as shown in SEQ ID NO: 18, FR2 comprising the amino acid sequence as shown in SEQ ID NO: 19, FR3 comprising the amino acid sequence as shown in SEQ ID NO: 20, and FR4 comprising the amino acid sequence as shown in SEQ ID NO: 21. A trivalent or larger antibody is preferable in order to activate TRAIL-R1. The antibody may be an artificial antibody as described above, such as a chimeric or humanized antibody.

Since an agonistic antibody against TRAIL-R1 induces apoptosis via TRAIL-R1, the antibody of the present invention can be used as an inducer of apoptosis.

ii) Anti-TRAIL-R2 Antibody

In the present invention, the term "anti-TRAIL-R2 single-chain antibody" refers to a single-chain antibody against TRAIL-R2 (TNF-related apoptosis-inducing ligand receptor 2; TRAIL receptor 2). The anti-TRAIL-R2 single-chain antibody used in the present invention is not particularly limited, provided that it can specifically bind to TRAIL-R2. An example of an anti-TRAIL-R2 single-chain antibody that can be used in the present invention is 4E6, which is described in WO 2011/098520. 4E6 is a single-chain VHH antibody derived from llama, and comprises CDR1 comprising the amino acid sequence as shown in SEQ ID NO: 15, CDR2 comprising the amino acid sequence as shown in SEQ ID NO: 16, and CDR3 comprising the amino acid sequence as shown in SEQ ID NO: 17.

It is particularly preferable that the fusion protein used in the present invention have agonistic activity of binding to TRAIL-R2 and inducing apoptosis. TRAIL-R2 induces apoptosis upon aggregation to form trimer or larger multimer. In order to activate TRAIL-R2, accordingly, it is particularly preferable that the fusion protein comprise 3 or more, 4 or more, 5 or more, or 6 or more, for example, 3, 4, 5, or 6 anti-TRAIL-R2 single-chain antibodies, as described above.

Since an agonistic antibody against TRAIL-R2 induces apoptosis via TRAIL-R2, the antibody of the present invention can be used as an inducer of apoptosis.

(3) Functional Peptide

The above fusion protein optionally contains one or more functional peptides. The term "functional peptide" used herein refers to a peptide having, in a living body or within cells, specific bioactivity such as enzymatic activity, catalytic activity, functions as a substrate, or biological inhibitory or enhancement activity (for example, cytotoxic activity). Specific examples thereof include a fluorescent protein or a luminescent protein, an enzyme, and an exotoxin.

Functional peptides may be derived from any biological species. Moreover, functional peptides may be either natural or unnatural. The term "natural functional polypeptide" refers to a peptide that exists in nature. On the other hand, the term "unnatural functional polypeptide" refers to a modified peptide prepared by introducing appropriate mutation(s) (such as the addition, deletion, and/or substitution of an amino acid(s)) into the amino acid sequence based on the amino acid sequence of a natural functional polypeptide, as long as the functional peptide does not lose its own unique functions.

The above fusion protein may contain 2 or more functional peptides. When the above fusion protein contains a plurality of functional peptides, however, the total molecular weight of the functional peptides is preferably 80 kDa or less, and preferably 40 kDa or less so that the overall molecular weight of the fusion protein does not become too large. When the above fusion protein contains 2 or more functional peptides, functional peptides may be of the same type or different types. Examples thereof include a functional peptide comprising an exotoxin in combination with an enzyme and an exotoxin in combination with a fluorescent protein or luminescent protein. When the above fusion protein contains 2 or more functional peptides, individual functional peptides may be directly linked, and they are preferably linked via appropriate linker peptide(s), so that each functional peptide is able to efficiently exhibit its unique functions. The length and the amino acid sequence of a linker peptide are not particularly limited, as long as it does not inhibit the functions of the functional peptide. A fusion protein can contain two or more different functional peptides, so that the fusion protein can impart different functions to a target substance recognized by a single-chain antibody.

The functional peptide(s) are preferably positioned on the C-terminal side of the above single-chain antibody, although the location is not particularly limited, as long as it is located on the C-terminal side of a signal peptide in a fusion protein.

Hereafter, the fluorescent protein or luminescent protein, the enzyme, and the exotoxin described above, which can function as functional peptides in the recombinant bacteria of the present invention, are specifically described.

(i) Fluorescent Protein or Luminescent Protein (Labeling Protein)

The type of fluorescent protein used as a functional peptide is not particularly limited, as long as the nucleotide sequence thereof is known. Such a fluorescent protein may be either natural or unnatural. For the reason described above, a fluorescent protein having a short amino acid sequence is preferable. Moreover, the excitation wavelength and the fluorescence wavelength are not particularly limited. These wavelengths may be adequately selected in accordance with situation and necessity. Specific examples of such fluorescent protein include CFP, RFP, DsRed, YFP, PE, PerCP, APC, and GFP.

Also, the type of a luminescent protein is not particularly limited, as long as the nucleotide sequence thereof is known. As in the case of the fluorescent protein described above, a luminescent protein may be either natural or unnatural, and a luminescent protein having a short amino acid sequence is preferable. A specific example of such luminescent protein is aequorin.

(ii) Enzyme

The type of enzyme used as a functional peptide is not particularly limited, as long as the nucleotide sequence thereof is known. Such an enzyme may be an enzyme that directly acts on a target substance or an enzyme that does not directly act thereon, but rather acts in an area around a target substance. Specific examples of the latter enzyme include luciferase and peroxidase (e.g., horseradish peroxidase) which contribute to luminescence. A fusion protein in which such an enzyme is linked to the above single-chain antibody can function as an immunoenzyme.

(iii) Exotoxin

The term "exotoxin" refers to a toxic protein that is secreted from bacteria. An exotoxin to be used herein may be of any type, as long as it has cytotoxic activity and the nucleotide sequence thereof is known. Examples of such an exotoxin include *Pseudomonas aeruginosa* toxin (*Pseudomonas* toxin; PT) and derivatives thereof such as exotoxin A prepared by removing a cell adhesion domain from PT, Diphtheria toxin (DT) and derivatives thereof, and Ricin and derivatives thereof (Brinkmann U. & Pastan I., 1994, Biochimica et Biophysica Acta, 1198 (1): 27-45). *Pseudomonas aeruginosa* exotoxin A is known to inhibit protein synthesis by inactivating EF-2 by ADP ribosylation and to exhibit a strong cytotoxic effect, after incorporation thereof into cancer cells. A fusion protein in which an exotoxin is linked to the above single-chain antibody can function as an immunotoxin.

1-2-2. Configuration of Expression Cassette

The term "expression cassette" as used herein refers to an expression system that contains the above fusion gene and brings the fusion gene to an expressible state as a fusion protein. The term "expressible state" as used herein refers to a situation in which a fusion gene is positioned under the control of elements required for gene expression so that the fusion gene contained in the expression cassette is able to be expressed within recombinant bacteria. Examples of elements required for gene expression include a promoter and a terminator.

Promoters to be used herein are not particularly limited, as long as such promoters can be functional within recombinant bacteria. Promoters derived from obligate anaerobic Gram-positive bacteria to be used are preferable. When *B. longum* (*Bifidobacterium*) is used as an obligate anaerobic gram-positive bacterium, an example thereof is the hup gene promoter (SEQ ID NO: 25) of *B. longum*. Furthermore, promoters differing in properties of expression control including an overexpression promoter, a constitutive promoter, a site-specific promoter, a stage-specific promoter, an inducible promoter, and the like are known. A promoter to be used for an expression cassette in the present invention may be any promoter without particular limitation. A promoter may be adequately selected, according to need. A preferable example thereof is an overexpression promoter or a constitutive promoter. A promoter is positioned on the 5' upstream of the initiation codon of the above fusion gene in the above expression cassette.

A terminator to be used herein is not particularly limited, as long as it can terminate the transcription of a gene transcribed by the above promoter within recombinant bacteria. An example of such a terminator includes the histone-like protein terminator (HUT) (SEQ ID NO: 26). A terminator to be used herein is preferably a terminator derived from the same biological species as that of a promoter, and it is more preferably a terminator that forms a pair with a promoter on the genome of the biological species from which the promoter is derived. A terminator is positioned on the 3' downstream of the termination codon of the above fusion gene, in the above expression cassette.

A vector containing an expression cassette can be introduced as an expression vector into the bacteria to stably express the above fusion protein within the recombinant bacteria. Alternatively, a vector may be inserted into the genome of the bacteria via homologous recombination. When an expression vector is used, a plasmid or the like can be used as a vector. A vector to be used herein is replicable within the recombinant bacteria of the present invention and contains an appropriate selection marker gene that is stably retained within the bacteria. A vector may be a shuttle vector that is replicable within other bacteria such as *Escherichia coli*. Examples thereof include pKKT427, pBESAF2, and pPSAB1. When a vector is inserted into the genome of recombinant bacteria, a fusion gene alone may be inserted into the genome of recombinant bacteria in an expressible state. Specifically, a fusion gene may be inserted under the control of an endogenous promoter and/or terminator of the recombinant bacteria.

An expression cassette may be monocistronic, which contains one fusion gene within a single expression cassette, or polycistronic, which contains 2 or more fusion genes.

1-3. Method for Producing Recombinant Obligate Anaerobic Gram-Positive Bacteria

The recombinant bacteria of the present invention can be produced using molecular genetic methods known in the art. In the case of the above fusion gene, for example, nucleic acids each encoding a signal peptide and single-chain antibody(ies) may be constructed using techniques described in Green and Sambrook, Molecular Cloning, 4th Ed., 2012, Cold Spring Harbor Laboratory Press or Ausubel et al., Short Protocols in Molecular Biology, 3rd Ed., A compendium of Methods from Current Protocols in Molecular Biology, 1995, John Wiley & Sons.

The single-chain antibody can be obtained with the use of the nucleotide sequence information of the gene encoding an antibody that binds to TRAIL-R1 or TRAIL-R2. The nucleotide sequence information of the antibody may be based on, for example, the above-described nucleotide sequences of CDRs and FRs.

When a new antibody against TRAIL-R1 or TRAIL-R2 is produced, a monoclonal antibody against TRAIL-R1 or TRAIL-R2 can be prepared in accordance with a method known in the art. A preparation example thereof is as described below.

Extracellular domains of target TRAIL-R1 or TRAIL-R2 are administered as immunogens to animals of the family Camelidae for immunization. If necessary, an adjuvant may be added for effective immunization. Examples of an adjuvant include commercially available complete Freund's adjuvant (FCA) and incomplete Freund's adjuvant (FIA), and these adjuvants can be used alone or in combination. A single dose of an immunogen solution may contain about 50 μg to 200 μg of the immunogen per animal above. The intervals for immunization are not particularly limited. After primary immunization, an immunized animal is boosted 2 to 10 times and preferably 5 to 7 times at intervals of several days to several weeks, and preferably 1 to 4 weeks. After primary immunization, the antibody titer in the serum of the immunized animal is measured repeatedly by ELISA (i.e., enzyme-linked immunosorbent assay) or other means. Subsequently, antibody-producing cells are collected from the immunized animal. Examples of antibody-producing cells include spleen cells, lymph node cells, and peripheral blood cells, with peripheral blood cells being preferable. RNA is extracted from peripheral blood cells, and cDNA is then synthesized using an oligo dT primer and a random 6-mer primer. From the cDNA, the gene of the variable region (Vim region) of the single-chain antibody of the family Camelidae is amplified by PCR, the above gene is incorporated into a phagemid vector such as pCANTAB6 (McCafferty J. et al., 1994, Appl. Biochem. Biotech., 47, 157-173), and the vector is then introduced into *Escherichia coli* TG1 by electroporation. The above *Escherichia coli* TG1 is infected with an M13K07 helper phage, the resultant phages are collected, and a library of expression phages with a single-chain antibody variable region ($V_{HH}$ region) of the family Camelidae is thus obtained. This is normally a library of $1 \times 10^7$ pfu or more.

Biopanning is performed to select phages expressing an antibody against a target antigen. Biopanning is a method for concentrating a phage specific to a target antigen, which involves reacting an antibody phage library with an immobilized target antigen, removing unbound phages by washing, eluting phages binding to the target antigen, infecting *Escherichia coli* with the phages for proliferation, and repeating these procedures 3 to 5 times. After re-infection of *Escherichia coli* TG1 with phages subjected to biopanning, TG1 clones containing Vim inserted pCANTAB phagemid vectors are isolated. TG1 clones are each infected with a KO7 helper phage, and cloned phages presenting the Vim antibody are thus obtained. Clones that react with the antigen are selected from among such phages. The nucleotide sequence of the antibody can be obtained from the phages thus obtained.

A fusion gene is inserted into the above expression cassette using a molecular genetic method so that the fusion gene can be expressed. An expression cassette is incorporated into a vector such as a plasmid, according to need. An expression cassette may be incorporated into a vector by, for example, a method that involves cleaving the 5' end and the 3' end of an expression cassette with appropriate restriction enzyme(s) and inserting the expression cassette into a corresponding restriction site such as a multicloning site within the vector. Further, when a vector is an expression vector that enables expression within the recombinant bacteria of the present invention, the above fusion gene can be inserted into the expression control region (e.g., a multicloning site between a promoter and a terminator within the vector) of the expression vector, so that the expression cassette and the target expression vector can be constructed at the same time. Regarding specific methods therefor, reference may be made to, for example, the method described in the literature of Green and Sambrook (2012) described above.

Recombinant bacteria of interest can be produced by introducing the above expression vector, expression cassette, or fusion gene into obligate anaerobic Gram-positive bacteria as drug delivery carriers. As a method for introducing an expression vector or the like into target obligate anaerobic Gram-positive bacteria, a molecular biological method known in the art can be employed. For example, a known method such as electroporation or a calcium phosphate method can be employed. Regarding specific methods therefor, reference may be made to, for example, the method described in the literature of Green and Sambrook (2012) described above.

2. Antitumor Agent

2-1. Overview

A second aspect of the present invention is an antitumor agent. According to the present invention, the term "antitumor agent" refers to a drug having cytotoxic activity against tumor cells, causing apoptosis of the cells, and, as a result, suppressing the proliferation of the tumor cells. The antitumor agent is required to have the beneficial effect of suppressing tumor cell proliferation, but it is not required to eradicate the tumor cells.

The antitumor agent of the present invention is characterized by comprising recombinant bacteria of the first aspect as an active ingredient. Regarding the antitumor agent of the present invention, the recombinant bacterium as an active ingredient grows only within tumors and secretes 3 or more anti-TRAIL-R1 single-chain antibodies and/or 3 or more anti-TRAIL-R2 single-chain antibodies within tumors, so that apoptosis can be efficiently induced in tumors, which leads to tumor regression.

2-2. Configuration

The antitumor agent of the present invention comprises the recombinant bacteria of the first aspect as an active ingredient, as described above. The recombinant bacteria in this case comprises the fusion gene encoding single-chain antibodies recognizing and binding to surface antigens of target tumor cells (i.e., TRAIL-R1) and/or a single-chain antibodies recognizing and binding to TRAIL-R2. Therefore, the recombinant bacteria as an active ingredient of the antitumor agent of the present invention secrete an extracellular secretory antitumor cell fusion protein.

Tumors targeted by the antitumor agent of the present invention may be any tumors, regardless of whether they are benign or malignant, provided that such tumors express TRAIL-R1 and/or TRAIL-R2. Examples of target tumors include brain tumors, thyroid cancer, oral cancer, esophageal cancer, gastric cancer, large bowel cancer, pharyngeal cancer, lung cancer, liver cancer, renal cancer, adrenal cancer, pancreatic cancer, biliary tract cancer, cervical cancer, uterine body cancer, ovarian cancer, mammary cancer, prostate cancer, bladder cancer, fibrosarcoma, mastocytoma, and melanoma.

When the recombinant bacteria of the present invention express a fusion gene, the expression product; that is, an extracellular secretory antitumor cell fusion protein, is secreted extracellularly. The secreted fusion protein binds to tumor cells as target substances through its single-chain antibody moiety, and induces apoptosis of the cells by multimerization of TRAIL-R1 and/or TRAIL-R2.

The antitumor agent comprises the recombinant bacteria of the present invention as an active ingredient in a viable state. The recombinant bacteria described in the first aspect of the present invention cannot grow and will eventually die at high oxygen concentrations. In a living body, accordingly, the recombinant bacterium can grow and survive only at sites with low oxygen partial pressure. Typical examples of such sites include central regions of tumors (solid cancer) observed in cases of advanced cancer or within the intestine. Therefore, the antitumor agent of the present invention can be an antitumor agent delivered to tumors with high selectivity when administered in vivo by injection or the like.

Furthermore, the antitumor agent of the present invention can be used in combination with other antitumor agent(s), as long as it does not inhibit or suppress the survival and the growth of the recombinant bacteria as an active ingredient and the expression and the secretion of the fusion protein.

In principle, the antitumor agent of the present invention can be formulated by a method known in the art on the assumption that the recombinant bacteria are maintained or preserved in a viable state. For example, the method described in Remington's Pharmaceutical Sciences (Merck Publishing Co., Easton, Pa.) can be employed. Specific methods for formulation vary depending on methods of administration. Methods of administration are classified roughly into oral administration and parenteral administration. In the case of the antitumor agent of the present invention, parenteral administration is preferable.

When the antitumor agent of the present invention is administered parenterally, a specific example thereof is administration by injection. When the antitumor agent of the present invention is administered via injection, the antitumor agent can be prepared as a suspension agent by mixing the recombinant bacteria with a pharmaceutically acceptable solvent and adding a pharmaceutically acceptable carrier, according to need.

A "pharmaceutically acceptable solvent" may be water, a pharmacologically acceptable aqueous solution other than water, or an oily fluid. Examples of an aqueous solution include a saline solution and an isotonic solution containing glucose and other auxiliary agents. Examples of auxiliary agents include D-sorbitol, D-mannose, D-mannitol, sodium chloride, low-concentration nonionic surfactants (e.g., polysorbate 80™, HCO-60), and polyoxyethylene sorbitan fatty acid esters. Examples of oily fluids include sesame oil and soybean oil. The solvent can also be used in combination with benzyl benzoate or benzyl alcohol as a solubilizing agent. Moreover, the solvent may be mixed with a buffering agent such as a phosphate buffer or a sodium acetate buffer, a soothing agent such as procaine hydrochloride, a stabilizer such as benzyl alcohol or phenol, or an antioxidant.

An injection may be formulated by adequately mixing an active ingredient with a pharmaceutically acceptable excipient, emulsifier, suspension, surfactant, stabilizer, pH adjusting agent, or the like in a unit dosage form required for a generally accepted pharmaceutical practice.

Examples of injection include intravascular injection, intralymphatic injection, intramuscular injection, intraperitoneal injection, and hypodermic injection. Based on a mechanism that the recombinant bacteria as an active ingredient of the antitumor agent of the present invention grow within a tumor and suppress the proliferation of such tumor cells, administration into the cardiovascular system (i.e., systemic administration such as intravascular injection or intralymphatic injection) is preferable when the tumor site is not identified. Examples of intravascular injection include intravenous injection and intraarterial injection. The antitumor agent of the present invention may be administered intravenously or intraarterially. On the other hand, when the position of a tumor site is identified, topical administration involving direct administration to a tumor may be employed, in addition to the aforementioned systemic administration.

When the antitumor agent of the present invention is administered orally, the antitumor agent may be supplemented with a pharmaceutically acceptable carrier, in addition to the recombinant bacteria that is an active ingredient.

The term "pharmaceutically acceptable carrier" refers to a substance that facilitates the formulation of a drug or the application of a drug to a living body and is added to the drug, so as to maintain the survival of the recombinant bacteria as an active ingredient, while refraining from inhibiting or suppressing the effect of the bacteria. Examples thereof include an excipient, a binder, a disintegrator, a filler, an emulsifier, a fluid modulator to be added, and a lubricant.

Examples of an "excipient" include sugars such as monosaccharides, disaccharides, cyclodextrins, and polysaccharides (specific examples thereof include, but are not limited to, glucose, sucrose, lactose, raffinose, mannitol, sorbitol, inositol, dextrin, maltodextrin, starch, and cellulose), metallic salts (e.g., sodium phosphate or calcium phosphate, calcium sulfate, and magnesium sulfate), citric acid, tartaric acid, glycine, low-, medium-, and high-molecular-weight polyethylene glycols (PEG), pluronic, and any combination thereof.

Examples of a "binder" include starch pastes prepared from corn, wheat, rice, or potato, gelatin, tragacanth, methylcellulose, hydroxypropyl methylcellulose, sodium carboxymethylcellulose, and polyvinylpyrrolidone.

Examples of a "disintegrator" include the aforementioned starches, carboxymethyl starch, crosslinking polyvinylpyrrolidone, agar, alginic acid or sodium alginate, and salts thereof.

Examples of a "filler" include the aforementioned sugars and/or calcium phosphate (e.g., tricalcium phosphate or dibasic calcium phosphate).

Examples of an "emulsifier" include a sorbitan fatty acid ester, a glycerin fatty acid ester, a sucrose fatty acid ester, and a propylene glycol fatty acid ester.

Examples of a "fluid modulator to be added" and a "lubricant" include silicate, talc, stearate, and polyethylene glycol.

In addition, the antitumor agent may comprise a taste and flavor corrigent, a suspension, a diluent, a surfactant, an extending agent, a humidifying agent, a moisturizing agent (e.g., glycerin and starch), an adsorbent (e.g., starch, lactose, kaolin, bentonite, and colloidal silicic acid), a disintegration-suppressing agent (e.g., saccharose, stearin, cocoa butter, and hydrogenated oil), a coating agent, a colorant, a preservative, an antioxidant, aroma chemicals, a flavoring agent, a sweetening agent, and a buffering agent, according to need. One, two, or more of the carriers mentioned above may be adequately used, according to need.

Examples of the dosage form of an oral vaccine agent include solids (e.g., tablets, pills, sublingual agents, capsules, and drops), granules, dust formulations, powders, and solutions. Furthermore, solids can be formulated into dosage forms via coating known in the art, such as sugar-coated tablets, encapsulated gelatin tablets, enteric-coated tablets, film-coated tablets, double layer tablets, and multilayer tablets, according to need. Specific shapes and sizes of such dosage forms are not particularly limited, as long as the shapes and the sizes are within the scope of the relevant dosage forms known in the art.

The content of the recombinant bacteria in the antitumor agent of the present invention may be any amount, provided that the bacteria is able to reach a target tumor in a viable and proliferative state via a single administration in principle and the bacteria would impose no or substantially no harmful side effects on the subject to which the agent is administered. Such contents vary depending on the types of target cells of the antitumor agent, cancer stages, tumor sizes, the number of tumor sites throughout the body, dosage forms of the antitumor agent, and methods for administration of the antitumor agent. The content is adequately determined in view of these conditions.

Objects to which the antitumor agent of the present invention is administered are subjects having tumors or subjects with the high possibility of having tumors. The term "subjects" as used herein refers to animals to which the antitumor agent of the present invention is administered. Examples thereof include mammals, preferably humans, dogs, cats, horses, mice, rats, rabbits, cattle, and monkeys, and more preferably humans.

2-3. Effects

Regarding the antitumor agent of the present invention, the recombinant bacteria as an active ingredient survive and proliferate only within tumors with low oxygen partial pressure and secrete antitumor cell fusion proteins. Therefore, the fusion proteins can be efficiently delivered to tumor cells and allowed to continuously act. Further, when the oxygen partial pressure in the tissue is increased by suppression of tumor cell proliferation and tumor regression due to the effects of the fusion proteins, the recombinant bacteria that are obligate anaerobic Gram-positive bacteria become inviable, and thus such bacteria can be automatically eliminated from the living body. Accordingly, a safer and more convenient therapeutic method in comparison with conventional bacteriotherapy can be provided, and it can exert antitumor effects against the solid cancer via intravenous administration of non-pathogenic obligate anaerobic bacteria alone without any other antitumor agents.

Since the antitumor agent of the present invention can be administered via intravenous injection, it is advantageous in terms of low levels of subject invasiveness.

3. Marker for Tumor Detection 3-1. Overview

A third aspect of the present invention is a marker for tumor detection. The term "marker for tumor detection" used in the present invention refers to a marker capable of detecting a tumor in vivo.

The marker for tumor detection of the present invention comprises the recombinant bacteria of the first aspect as an active ingredient. With the use of the marker for tumor detection of the present invention, the positions or the sizes of tumors in vivo can be observed because the recombinant bacteria as an active ingredient grow only within tumors and secrete an enzyme, a fluorescent protein, or a luminescent protein within tumors.

3-2. Configuration

The basic configuration is in accordance with that of the antitumor agent of the second aspect. Accordingly, differences with the above antitumor agent are mainly explained herein, and explanations of overlapping configurations are omitted in principle. The marker for tumor detection of the present invention comprises the recombinant bacteria of the first aspect as an active ingredient, as described above. The recombinant bacterium in this case is characterized in that a fusion gene encodes single-chain antibodies recognizing and binding to a surface antigen of target tumor cells, and a functional peptide encodes a labeling protein or a protein inducing labeling. Examples of a labeling protein include the fluorescent protein and the luminescent protein described above. Examples of a protein inducing labeling include enzymes (luciferase and peroxidase), the substrates of which are luminophores or fluorophores, such as luciferin and luminol. Therefore, the recombinant bacterium as an active ingredient of the marker for tumor detection of the present invention secretes an extracellular secretory antitumor cell immunomarker (immunolabel).

When the recombinant bacteria of the present invention express a fusion gene, the expression product; that is, an extracellular secretory antitumor cell immunomarker, is secreted extracellularly. The secreted immunomarker binds to TRAIL-R1 or TRAIL-R2 on tumor cells that are target substances with its single-chain antibody moiety, and thus the cells are labeled. Specifically, when a functional peptide is a labeling protein such as a luminescent protein or a fluorescent protein, tumor cells are directly labeled with the labeling protein linked with the single-chain antibody moiety. On the other hand, when a functional peptide is an enzyme, tumor cells are enzymatically labeled with the enzyme linked to the single-chain antibody moiety.

The marker for tumor detection of the present invention can be used in combination with the antitumor agent of the second aspect. In this case, the recombinant bacteria as active ingredients may be the same as or different from the recombinant bacteria that secrete the marker for tumor detection and the antitumor agent separately as individual molecules. Specifically, the recombinant bacteria may secrete different fusion proteins containing single-chain antibodies that recognize the same target substance. Alternatively, the recombinant bacteria may secrete one fusion protein containing an exotoxin and a labeling protein or an enzyme in its functional protein moiety. In such cases, the same tumor cells can be labeled and damaged by the effects of the exotoxin.

Moreover, the marker for tumor detection can be used in combination with other antitumor agents, as long as they do not inhibit or suppress the survival and the growth of the recombinant bacterium as an active ingredient and the expression and the secretion of the immunomarker.

3-3. Detection

When the marker for tumor detection of the present invention is administered to a subject who has a tumor, the recombinant bacteria as an active ingredient proliferate within the tumor, and an antitumor cell immunomarker is secreted. Tumor cells are labeled with the secreted immunomarker. The labeled tumor cells are detected by luminescence or fluorescence emitted by the labeling protein itself, when the immunomarker is a labeling protein such as a luminescent protein or a fluorescent protein. In the case of enzymatic labeling, luminescence or fluorescence resulting from an enzymatic reaction of a substrate such as luciferin administered in vivo may be detected. Methods for detecting an immunomarker are not particularly limited. Since many tumors are present within a living body, such tumors may be exposed by surgery such as laparotomy to detect an immunomarker. An immunomarker may also be detected noninvasively through detection of luminescence or fluorescence in vivo from outside the body. A noninvasive method involving detection from outside the body is preferable. An example of such a method that can be used herein for detecting luminescence or fluorescence derived from an immunomarker from outside the body is, but is not limited to, an in vivo bioimaging method. For example, an immunomarker can be detected by the methods described in Katz, M. H. et al., 2003, Cancer Res. 63: 5521-5525, Schmitt, C. A. et al., 2002, Cancer Cell, 1: 289-298, and Katz, M. H. et al., 2003, J. Surg. Res., 113: 151-160. Such detection can also be performed using a commercially available IVIS Imaging System (Caliper) or an apparatus similar thereto.

3-4. Effects

With the use of the marker for tumor detection of the present invention, the positions or the sizes of tumors in vivo can be observed from outside the living body based on an immunomarker. Further, with the use of the marker for tumor detection in combination with the antitumor agent of the second aspect of the present invention, the immunotoxin suppresses tumor cell proliferation, and tumor regression or the therapeutic effects can be monitored over time by detecting tumors in vivo from outside the living body using the immunomarker.

EXAMPLES

Example 1

Preparation of Anti-Human TRAIL-R2 Gene Expression Cassette to be Expressed in *Bifidobacterium*

(1) Gene Expression Cassette of Anti-hTRAIL-R2 VHH Antibody Tetramer (4E6 Tetramer) to be Expressed in *Bifidobacterium*

A gene (SEQ ID NO: 1) was prepared via DNA synthesis using the promoter region derived from the *B. longum* hup gene (SEQ ID NO: 25), the usp secretory signal sequence derived from the *B. longum* (SEQ ID NO: 29), DTY (the insertion sequence following the signal sequence), the amino acid sequence of 4E6 disclosed in WO 2011/098520, the linker peptide $(GGSGG)_2$ derived from the 8C7 EGFP gene (SEQ ID NO: 28), and the histone-like protein-derived terminator (HUT) (SEQ ID NO: 26), and DNA encoding the His-Tag sequence was added to the C terminus.

(2) Gene Expression Cassette of Fusion Protein of Anti-hTRAIL-R2 VHH Antibody Dimer and *Pseudomonas aeruginosa* Exotoxin A Subunit (4E6 Dimer Toxin) to be Expressed in *Bifidobacterium*

A gene (SEQ ID NO: 2) was prepared via DNA synthesis using the promoter region derived from the hup gene of *B. longum* (SEQ ID NO: 25), the usp secretory signal sequence derived from the *B. longum*, DTY (the insertion sequence following the signal sequence) (SEQ ID NO: 29), the amino acid sequence of 4E6 disclosed in WO 2011/098520, the linker peptide (GGSGG)$_2$ derived from the 8C7 EGFP gene (SEQ ID NO: 28), *Pseudomonas aeruginosa* exotoxin A (the DNA sequence of exotoxin A encoded by pJH8 (purchased from ATCC)), and the histone-like protein-derived terminator (HUT) (SEQ ID NO: 26), and DNA encoding the His-Tag sequence added to the C terminus.

(3) Gene Expression Cassette of Fusion Protein of Anti-hTRAIL-R2 VHH Antibody Dimer and Green Fluorescent Protein (4E6 Dimer EGFP) to be Expressed in *Bifidobacterium*

A DNA sequence (SEQ ID NO: 3) was prepared using the promoter region derived from the hup gene of *B. longum* (SEQ ID NO: 25), the usp secretory signal sequence derived from the *B. longum* (SEQ ID NO: 29), DTY (the insertion sequence following the signal sequence), and the histone-like protein-derived terminator (HUT) (SEQ ID NO: 26), and adding a DNA sequence encoding the linker peptide (GGSGG)$_2$ derived from the 8C7 EGFP gene (SEQ ID NO: 28), the EGFP gene (Zhang G. et al., 1996, Biochem Biophys Res Commun, 227 (3):707-711), and the His-Tag sequence to the 3' terminus of the 4E6 dimer gene.

Example 2

Preparation of Cultured *Drosophila* Cells that Express and Secrete hTRAIL-R1:Fc, hTRAIL-R2:Fc, and mTRAIL-R2:Fc and Purification of the Recombinant Proteins (1) Preparation of Gene Expression Cassette
(1-1) Gene Expression Cassette of Human TRAIL-R1:Alpaca Fc (hTRAIL-R1:Fc) to be Expressed in Cultured *Drosophila* Cells DNA comprising the KpnI site, the consensus sequence for translation initiation (Cavener D. R., 1987, Nucleic Acids Res. 15, 1353-1361), the Bip secretory signal (Life Technologies), the hTRAIL-R1 extracellular region (Accession No. AAC51226, amino acids 109 to 239), the IEGRMD linker (SEQ ID NO: 27), the *Lama pacos* (alpaca) IgG1 Fc (Accession No. AM773729, amino acids 102 to 335), the His-Tag sequence, the termination codon, and the XhoI site was synthesized (SEQ ID NO: 4).

(1-2) Gene Expression Cassette of Human TRAIL-R2:Alpaca Fc (hTRAIL-R2:Fc) to be Expressed in Cultured *Drosophila* Cells DNA comprising the KpnI site, the consensus sequence for translation initiation (Cavener D. R., 1987, Nucleic Acids Res., 15, 1353-1361), the Bip secretory signal (Life Technologies), the hTRAIL-R2 extracellular region (Accession No. Q6FH58, amino acids 54 to 182), the IEGRMD linker (SEQ ID NO: 27), *Lama* pacos (alpaca) IgG1 Fc (Accession No. AM773729, amino acids 102 to 335), the His-Tag sequence, the termination codon, and the XhoI site was synthesized (SEQ ID NO: 5).

(1-3) Gene Expression Cassette of Mouse TRAIL-R2: Alpaca Fc (mTRAIL-R2:Fc) to be Expressed in Cultured *Drosophila* Cells DNA comprising the KpnI site, the consensus sequence for translation initiation (Cavener D. R., 1987, Nucleic Acids Res. 15, 1353-1361), the Bip secretory signal (Life Technologies), the mTRAIL-R2 extracellular region (Accession No. Q9QZM4, amino acids 52 to 177), the IEGRMD linker (SEQ ID NO: 27), *Lama pacos* (alpaca) IgG1 Fc (Accession No. AM773729, amino acids 102 to 335), the His-Tag sequence, the termination codon, and the XhoI site was synthesized (SEQ ID NO: 6).

Figure 4:
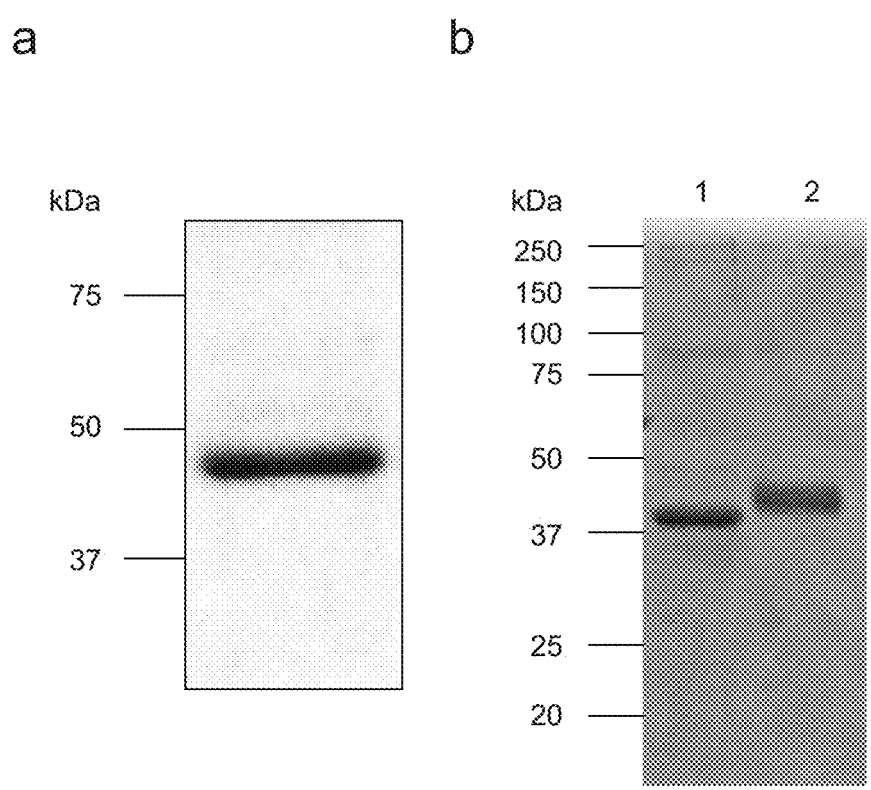
FIG. 4 shows SDS-PAGE (SDS polyacrylamide gel electrophoresis) images for purified hTRAIL-R1:Fc (a), hTRAIL-R2:Fc (b (1)), and mTRAIL (mouse TRAIL)-R2:Fc (b (2)).

(2) Preparation of Cultured *Drosophila* Cells that Express and Secrete hTRAIL-R1:Fc, hTRAIL-R2:Fc, and mTRAIL-R2:Fc and Purification of the Recombinant Proteins In order to obtain fusion proteins of extracellular regions of hTRAIL-R1, hTRAIL-R2, or mTRAIL-R2 and an Fc of alpaca IgG1, vectors that express and secrete these recombinant proteins in S2 cells, which are cultured *Drosophila* cells, were constructed (i.e., pAc5.1/hTRAIL-R1-Fc, pAc5.1/hTRAIL-R2-Fc, and pAc5.1/mTRAIL-R2-Fc). The gene expression cassettes that express and secrete recombinant proteins in S2 cells were inserted between the KpnI site and the XhoI site of the pAc5.1/V5-HisA plasmid (Life Technologies). The pAc5.1/V5-HisA plasmid and the pCoHygro plasmid (Life Technologies) containing a hygromycin resistance gene were introduced into the S2 cell at the ratio of 19:1 by the calcium phosphate method. The cells were cultured in Schneider's *Drosophila* Medium (Life Technologies) containing 300 µg/ml hygromycin (Life Technologies) and 10% fetal bovine serum (Tissue Culture Biologicals) to obtain the drug-resistant cells. The drug-resistant cells (1×10$^7$ cells/ml) were cultured in Express Five SFM (Life Technologies) containing 20 mM glutamine, and the culture supernatant was recovered after cultivating for 7 days. The recombinant proteins were purified using TALON resin (TAKARA BIO INC.). Specifically, the culture supernatant was added to a column filled with TALON resin, the column was washed with a wash buffer (25 mM HEPES, pH 7.4, 0.3 M NaCl, 5 mM imidazole), and recombinant proteins were eluted with an elution buffer (25 mM HEPES, pH 7.4, 0.3 M NaCl, 150 mM imidazole). The purified proteins were subjected to SDS-polyacrylamide electrophoresis and stained with Coomassie Brilliant Blue (CBB) R-250 (Bio-Rad), so as to confirm that the proteins had been purified (FIG. 4).

Example 3

Expression, Purification, and Binding Activity of Recombinant 4E6 Monomeric Protein in *E. coli* BL21 (DE3)

(1) Preparation of Gene Expression Cassette of Anti-hTRAIL-R2 VHH Antibody/Myc-Tag (4E6 Monomer) to be Expressed in *E. coli*

On the basis of the amino acid sequence information regarding the 4E6 VHH monomer disclosed in WO 2011/098520, a gene to be expressed in *E. coli* was prepared via DNA synthesis (SEQ ID NO: 7).

(2) Expression of 4E6 Monomer in *E. coli* and Purification Thereof

Figure 5:
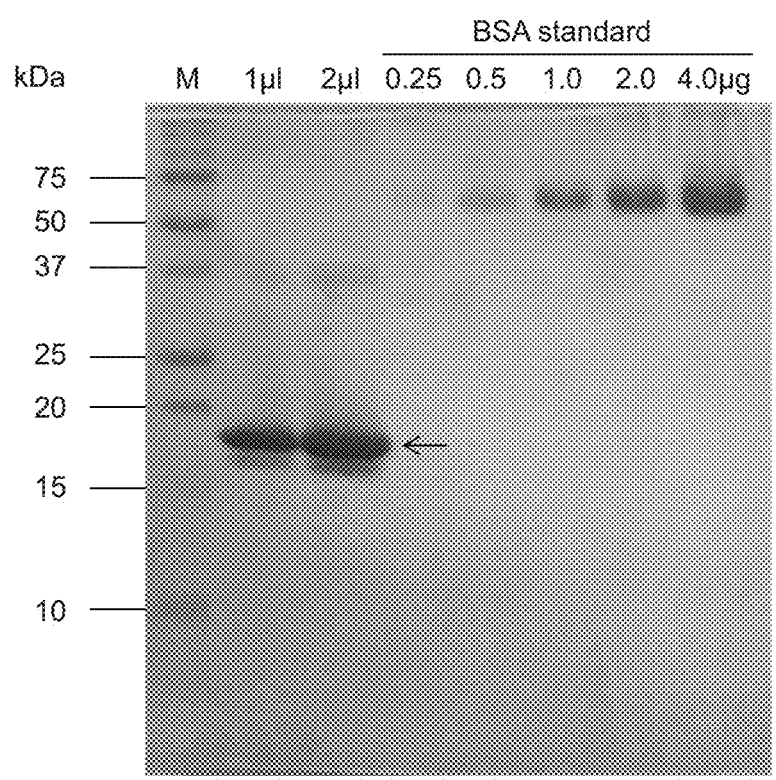
FIG. 5 shows an SDS-PAGE image for the purified 4E6 monomer. An arrow indicates the 4E6 monomer.

A vector expressing a 4E6 monomer was obtained by inserting the gene cassette between the NdeI site and the NotI site of pET22b(+). This expression vector (Plasmid DNA) was introduced into *E. coli* BL21Star™ (DE3) One Shot (Life Technologies). In accordance with the attached instructions, recombinant *E. coli* cells were cultured in 100 ml of 2YT medium containing 100 µg/ml ampicillin (Sigma-Aldrich) at 37° C., and 0.5 mM IPTG (isopropyl-β-thiogalactopyranoside, TAKARA BIO INC.) was added thereto when OD$_{600}$ reached 0.4 to 0.5, followed by cultivation at 30° C. for 3 hours. Following the cultivation, *E. coli* cells were recovered and resuspended in 10 ml of an extraction buffer (50 mM Na phosphate, pH 7.8, 300 mM NaCl, EDTA-free protease inhibitor cocktail, Roche). The cells were disrupted by ultrasonication on ice using Sonifier 250 (Branson) at the output control of 2 and the duty cycle of 80% for 1 minute twice. After the treatment, the suspension was centrifuged at 15,000 rpm and 4° C. for 20 minutes, and the supernatant was recovered. The fusion protein was purified with the use of the HisTrap column (GE Healthcare, U.K.). The centrifuged supernatant of the ultrasonicated suspension was directly applied to the HisTrap column, the column was washed with a binding buffer (20 mM sodium phosphate, 0.5 M NaCl, 20 mM imidazole, pH 7.4), and the fusion protein was then eluted with an eluate containing 500 mM imidazole. The purified sample was subjected to 15% SDS-polyacrylamide gel electrophoresis and then stained with CBB. The purified 4E6 monomeric protein was observed at approximately 15 KDa, and the concentration of the 4E6 monomer was estimated by comparing the results of staining of BSA (bovine serum albumin). As a result, the concentration of the 4E6 monomer was found to be about 3 µg/µl (FIG. 5).

Figure 6:
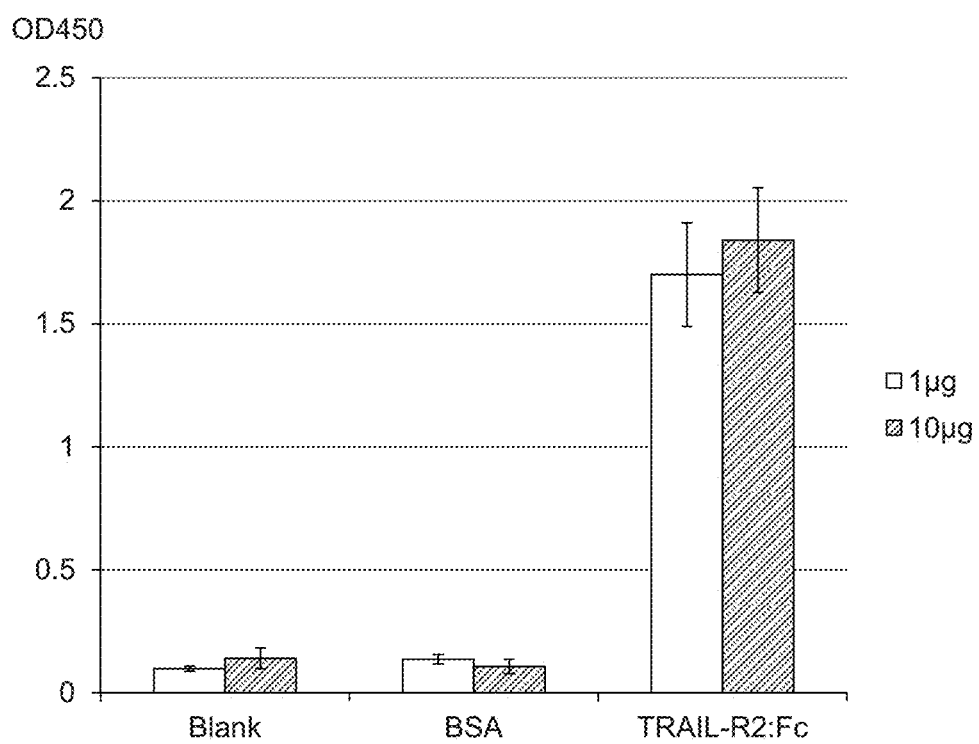
FIG. 6 shows binding activity of the 4E6 monomer to the hTRAIL-R2:Fc antigen measured by ELISA.

(3) Verification of Binding Activity of 4E6 Monomer to hTRAIL-R2:Fc Antigen Via ELISA hTRAIL-R2:Fc was prepared as described in Example 2. 0.1 M NaHCO$_3$ (Blank), 0.1 M NaHCO$_3$ containing 1 µg/ml or 10 µg/ml BSA (BSA negative antigen), or 0.1 M NaHCO$_3$ containing 1 µg/ml or 10 µg/ml hTRAIL-R2:Fc was added to a 96-well Immuno plate (Nunc) at 50 µl/well, and the plate was left at 4° C. overnight. SuperBlock-PBS (Thermo Scientific) was added thereto at 350 µl/well, and the plate was left at room temperature for 1 hour. The plate was washed with PBS-T (phosphate-buffered saline containing 0.05% Tween 20) at 400 µl/well, SuperBlock-PBS containing 1 µg/ml of 4E6 monomer was added thereto at 40 µl/well, and the reaction was allowed to proceed at room temperature for 1 hour. The plate was washed again three times with PBS-T at 400 µl/well, the anti-Myc mouse monoclonal antibody 9E10 (Santa Cruz Biotechnology) diluted 500-fold with SuperBlock-PBS was added thereto at 40 µl/well, and the reaction was allowed to proceed at room temperature for 1 hour. The plate was washed three times with PBS-T at 400 µl/well, the anti-mouse IgG goat antibody HRP was added thereto at 40 µl/well, and the plate was left at room temperature for 1 hour. Then, the plate was washed three times with PBS-T at 400 µl/well, a TMB reagent (Wako Pure Chemical Industries, Ltd.) was added thereto at 50 µl/well, the reaction was allowed to proceed for approximately 10 minutes, and the reaction was then terminated with 0.5 M sulfuric acid. Then, the absorbance at 450 nm was measured, and the mean and the standard deviation of the measurements performed in triplicate were calculated. The purified 4E6 monomeric protein specifically bound to hTRAIL-R2:Fc (FIG. 6).

(4) Measurement of Dissociation Constant (KD) Between 4E6 Monomer and hTRAIL-R2 ECD (Extracellular Domain)

Binding affinity between the 4E6 monomer and hTRAIL-R2:Fc (see Example 2) was analyzed via surface plasmon resonance technology using Biacore X-100 (GE Healthcare). Measurement was carried out via multi-cycle kinetics analysis in accordance with the Biacore X-100 instructions by adding the 4E6 monomer at concentrations of 0.919 nM, 1.838 nM, 3.675 nM, 7.35 nM, 14.7 nM, 29.4 nM, 58.8 nM, and 117.6 nM.

Figure 7:
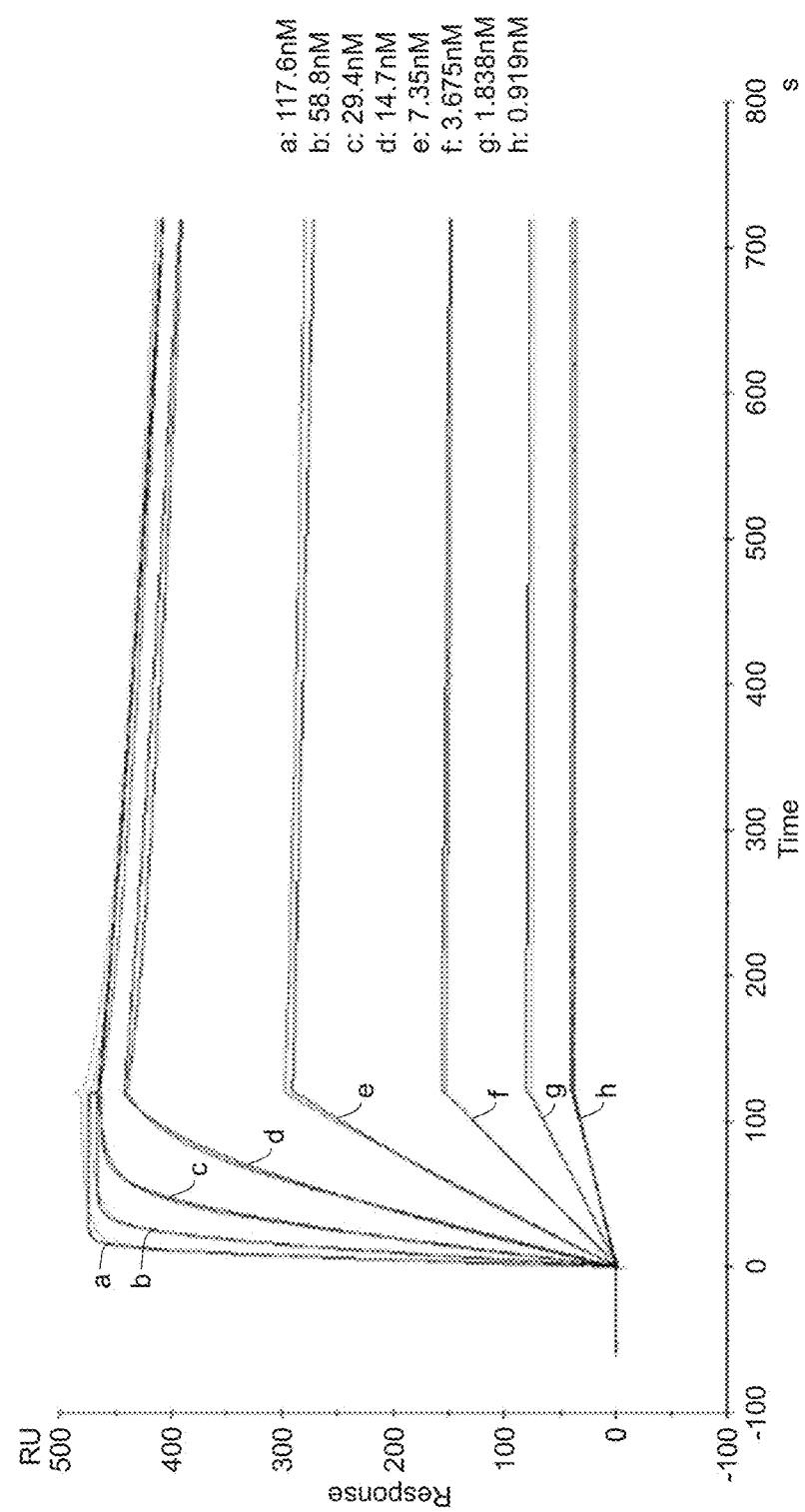
FIG. 7 shows the results of measurement of the dissociation constant between the 4E6 monomer and the hTRAIL-R2:Fc antigen using Biacore X-100.

FIG. 7 shows a sensorgram and fitting curves at each concentrations. The KD value between the 4E6 monomer and the recombinant human TRAIL-R2:Fc antigen was $7.5 \times 10^{-11}$ M.

Example 4

Obtaining Novel Anti-hTRAIL-R1 VHH Antibody (4P6 Monomer)

(1) Isolation of Novel Anti-hTRAIL-R1 VHH Antibody (4P6 Monomer) Gene

Since the anti-TRAIL-R1 VHH antibody has not been known, it was prepared in the following method. Specifically, the gene of VHH antibody that binds to hTRAIL-R1: human Fc (R&D Systems) was isolated via phage display with reference to the document of Maass et al. (J. Immunol. Methods, 2007, 324, 13-25). Alpaca was immunized with 100 µg of hTRAIL-R1:alpaca Fc six times at intervals of 1 to 2 weeks, leukocytes were recovered 8 weeks later, and RNA was extracted using RNeasy (Qiagen, Venlo, Netherland). cDNA was synthesized from this RNA with an oligo dT primer and a random 6-mer primer using the PrimeScriptII 1$^{st}$ strand cDNA synthesis kit (TAKARA BIO INC.). The VHH antibody gene was amplified via PCR using PrimeSTAR GXL DNA polymerase (TAKARA BIO INC.), and PCR was carried out via a cycle of 95° C. for 1 minute and 25 cycles of 98° C. for 10 seconds, 55° C. for 15 seconds, and 68° C. for 1 minute. The amplified product was subjected to a PCR procedure comprising a cycle of 95° C. for 1 minute and 20 cycles of 98° C. for 10 seconds, 60° C. for 15 seconds, and 68° C. for 1 minute in the same manner, so as to amplify the antibody gene. PCR was carried out using primers having the primer DNA sequence 1 (SEQ ID NO: 8) and the primer DNA sequence 2 (SEQ ID NO: 9). The sequence of the isolated antibody gene (4P6) was determined via cycle sequencing using the BigDye Terminator v3.1 (Life Technologies). As a result, the isolated antibody was found to comprise CDR1 comprising the amino acid sequence as shown in SEQ ID NO: 22, CDR2 comprising the amino acid sequence as shown in SEQ ID NO: 23, and CDR3 comprising the amino acid sequence as shown in SEQ ID NO: 24.

(2) Preparation of Gene Expression Cassette of 4P6 Monomer to be Expressed in Cultured *Drosophila* Cells DNA comprising the KpnI site, the consensus sequence for translation initiation (Cavener D. R., 1987, Nucleic Acids Res. 15, 1353-1361), the Bip secretory signal (Life Technologies), the 4P6 gene, the His-Tag sequence, the Myc-Tag sequence, the termination codon, and the XhoI site was synthesized.

Figure 8:
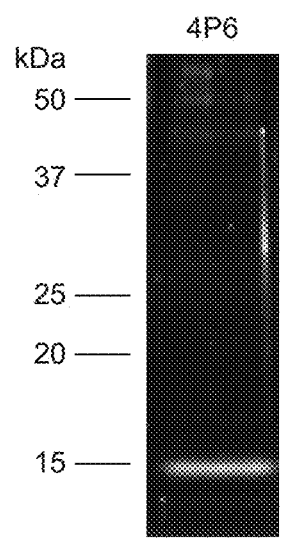
FIG. 8 shows an SDS-PAGE image for the purified 4P6 monomer.

(3) Preparation of Cultured *Drosophila* Cells that Express and Secrete Anti-hTRAIL-R1 VHH Antibody Monomer (4P6 Monomer) and Purification of the Recombinant Protein The gene expression cassette prepared in the above (2) was inserted between the KpnI site and the XhoI site of the pAc5.1/V5-HisA plasmid (Life Technologies), so as to prepare a vector (i.e., pAc5.1/4P6 monomer) that allows expression and secretion of the 4P6 monomer in cultured *Drosophila* cells (i.e., S2 cells). This plasmid and the pCoHygro plasmid containing a hygromycin resistance gene were introduced into the S2 cells at the ratio of 19:1 by the calcium phosphate method. The cells were cultured in the Schneider's *Drosophila* Medium (Life Technologies) containing 300 µg/ml hygromycin (Life Technologies) and 10% fetal bovine serum to obtain the drug-resistant cells. The drug-resistant cells were cultured in Express Five SFM (Life Technologies) containing 20 mM glutamine, and the culture supernatant was obtained. The 4P6 monomer was purified using the HisTrap column (GE Healthcare). The purified protein was subjected to 12.5% SDS-polyacrylamide gel electrophoresis and then stained with the Oriole Fluorescent Gel Stain (Bio-Rad) (FIG. 8).

Example 5

Measurement of Binding Specificity of Anti-hTRAIL-R1 VHH Antibody Monomer (4P6 Monomer) and Affinity Thereof with hTRAIL-R1

(1) Analysis of Binding Specificity of 4P6 Monomer and 4E6 Monomer Via ELISA

Figure 9:
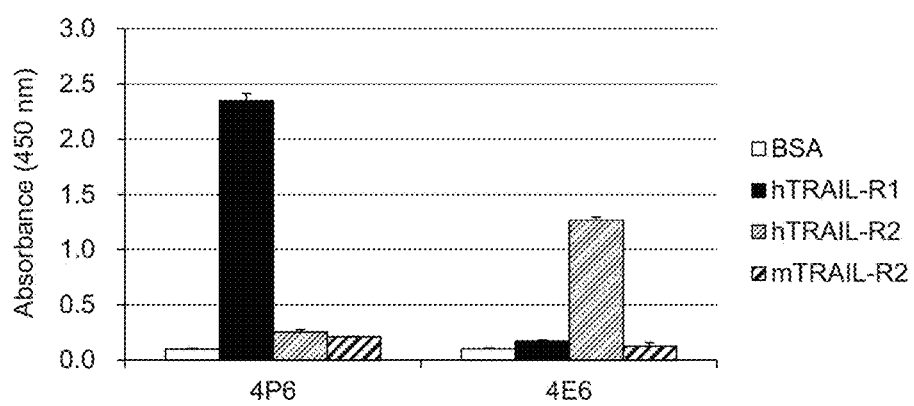
FIG. 9 shows the results of ELISA assays for binding specificities of the 4P6 monomer and 4E6 monomer.

Whether or not the 4P6 monomer selectively binds to TRAIL-R1 was investigated via ELISA. 50 µl each solutions of hTRAIL-R1:Fc, hTRAIL-R2:Fc, mTRAIL-R2:Fc (see Example 2), or bovine serum albumin dissolved in 0.1 M NaHCO$_3$ at 1 µg/ml was added to the 96-well Nunc Immuno plate (Thermo Scientific), and the resultant was left at 4° C. overnight. 300 µl of SuperBlock (TBS) Blocking Buffer (Thermo Scientific) was added and the resultant was left at room temperature for 1 hour. After the solutions were removed from the wells, the 4P6 monomer or 4E6 monomer dissolved at 10 µg/ml in a blocking buffer was added at 50 µl/well, and the resultant was left at room temperature for 1 hour. After the plate was washed three times with PBS containing 0.05% Tween 20, 50 µl of the 9E10 anti-Myc antibody (Santa Cruz Biotechnology) dissolved at 67 ng/ml in a blocking buffer was added thereto, and the resultant was left at room temperature for 1 hour. The resultant was washed three times, 50 µl of anti-mouse IgG HRP dissolved in a blocking buffer was added thereto, and the resultant was left at room temperature for 1 hour. The resultant was washed three times, 50 µl of a TMB solution (Wako Pure Chemical Industries, Ltd.) was added thereto, and the resultant was left at room temperature for 10 minutes. 50 µl of 0.5 M sulfuric acid was added and the absorbance at 450 nm was measured. 2 wells per samples were analyzed, and the average and the error of the measured value were calculated. It was confirmed that the 4P6 monomer specifically binds to hTRAIL-R1, and the 4E6 monomer specifically binds to hTRAIL-R2 (FIG. 9).

(2) Measurement of Dissociation Constant Between Anti-hTRAIL-R1 VHH Antibody Monomer (4P6 Monomer) and hTRAIL-R1 ECD (Extracellular Domain)

Figure 10:
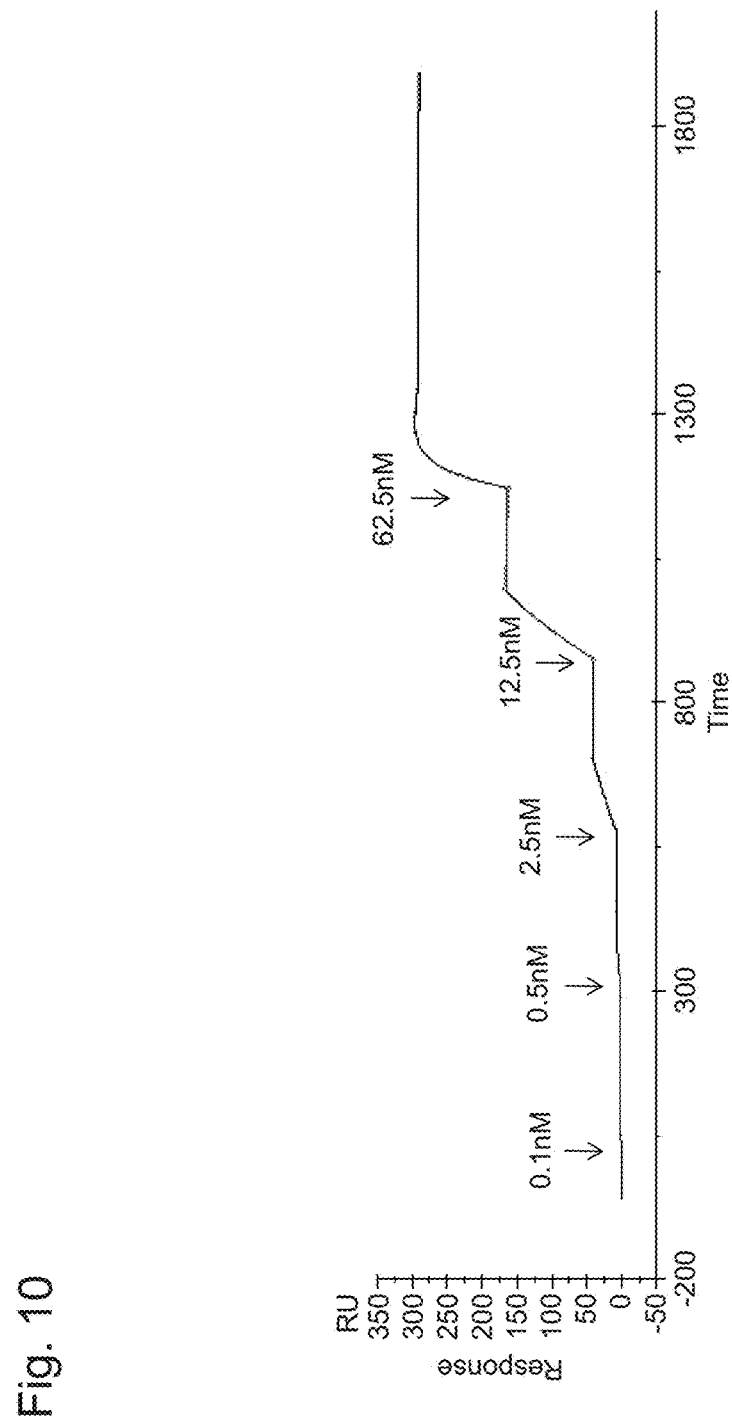
FIG. 10 shows the results of measurement of the dissociation constant between the 4P6 monomer and the hTRAIL-R1:Fc antigen using Biacore X-100.

Binding affinity between the 4P6 monomer and recombinant human TRAIL-R1 ECD was analyzed via surface plasmon resonance technology using Biacore X-100 (GE Healthcare). hTRAIL-R1:Fc (see Example 2) was fixed on a sensor chip (CMS) at approximately 1,000 RU. Measurement was carried out via single-cycle kinetics analysis in accordance with the Biacore X-100 instructions by successively adding the 4P6 monomer at concentrations of 0.1 nM, 0.5 nM, 2.5 nM, 12.5 nM, and 62.5 nM. FIG. 10 shows a sensorgram and a fitting curve. The KD value (dissociation constant) was $3.4 \times 10^{-11}$ M.

(3) Antagonistic Activity of 4P6 Monomer and 4E6 Monomer

Figure 11:
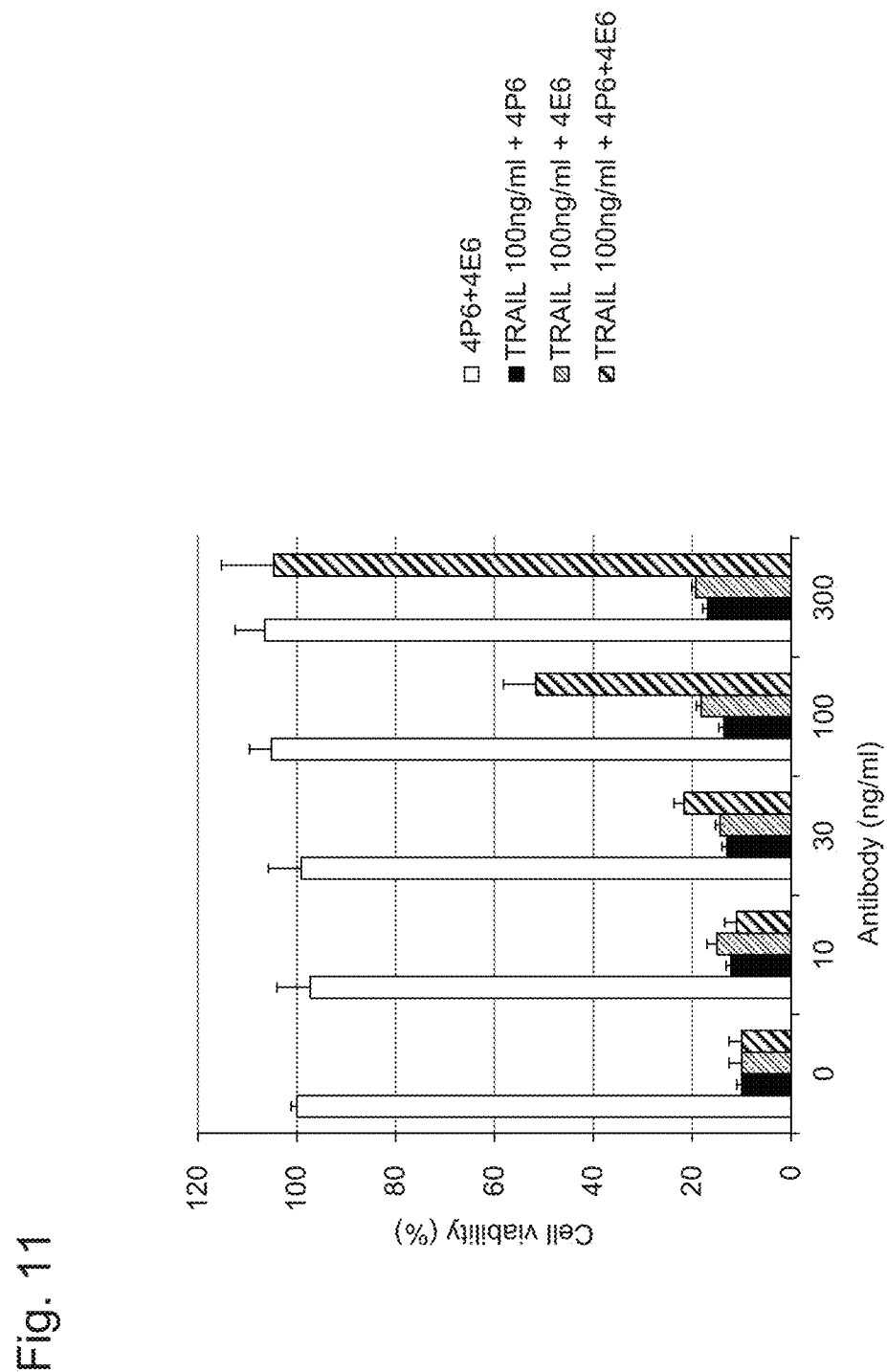
FIG. 11 shows antagonistic activities of the 4P6 monomer and 4E6 monomer.
Figure 12:
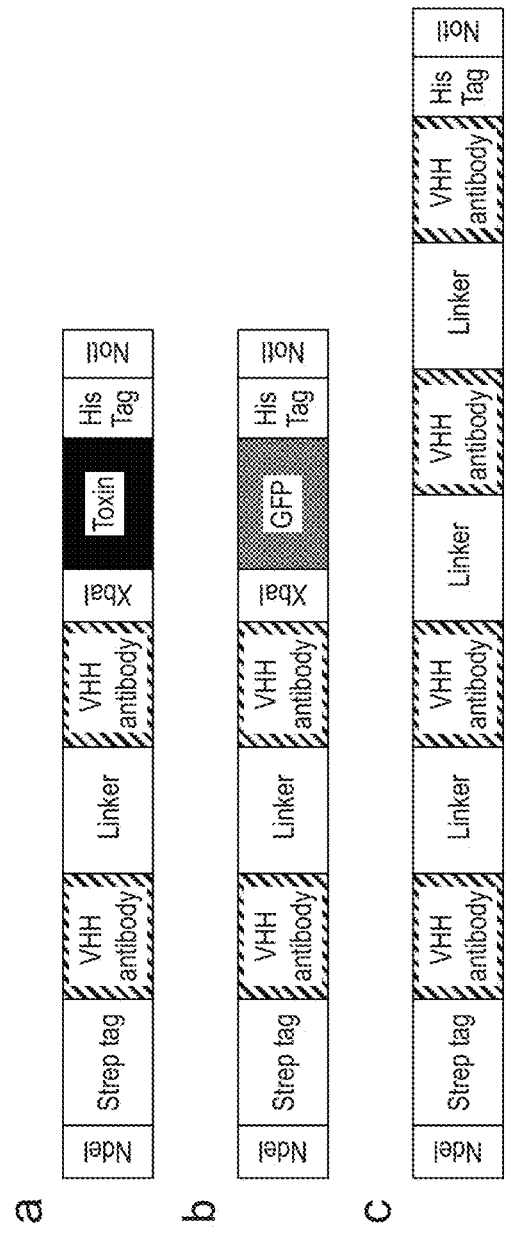
FIG. 12 schematically shows the gene structure of the 4E6 dimer toxin (a), the 4E6 dimer EGFP (b), and the 4E6 tetramer (c) expressed in $E.\ coli$.
Figure 13:
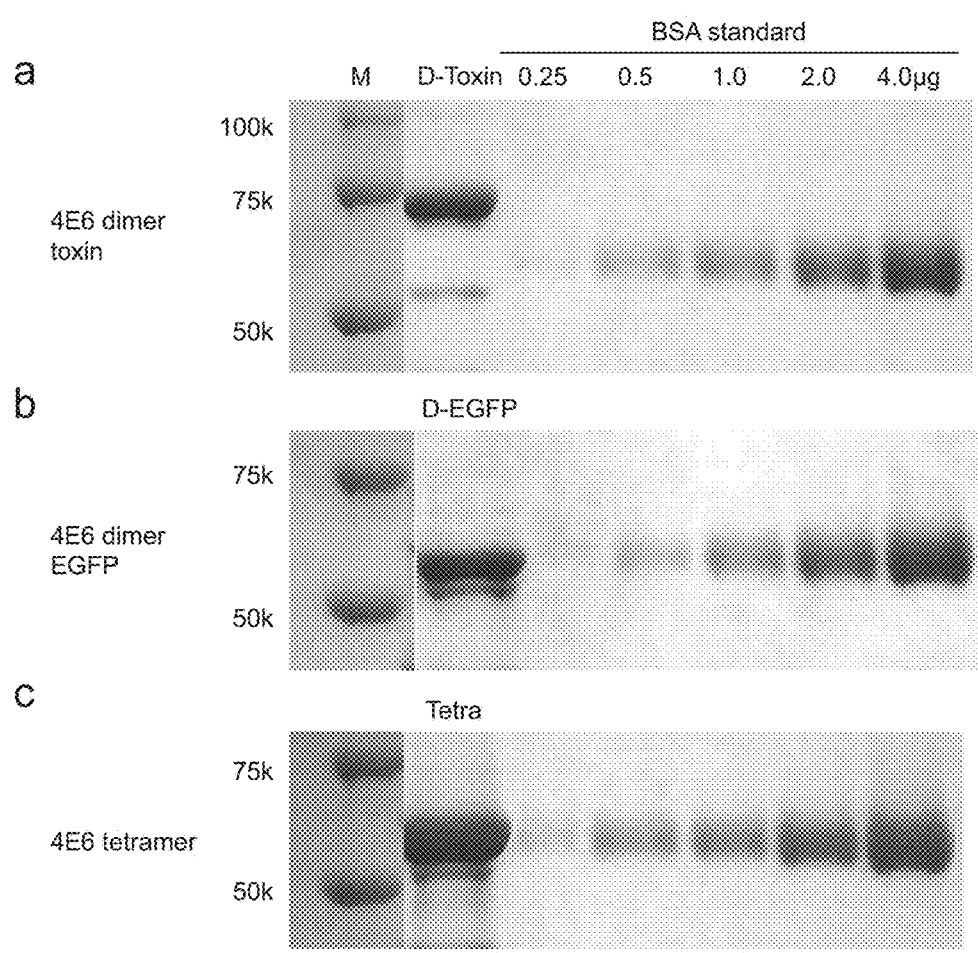
FIG. 13 shows SDS-PAGE images for purified recombinant proteins (a: 4E6 dimer toxin; b: 4E6 dimer EGFP; and c: 4E6 tetramer) expressed in $E.\ coli$.

Whether or not the 4P6 monomer exerts antagonistic activity against hTRAIL that binds to hTRAIL-R1 of cancer cells and induces apoptosis was analyzed. Human colon cancer cells (Colo205 cells) were suspended in RPMI 1640 medium (Sigma) supplemented with 10% fetal bovine serum (Tissue Culture Biologicals), and the cells were added to a Falcon 96-well culture plate (Becton, Dickinson and Company) at $3 \times 10^3$ cells/50 µl medium/well. The cells were cultured overnight, and 50 µl each of media containing TRAIL at the final concentration of 100 ng/ml, as well as the 4P6 monomer, and the anti-hTRAIL-R2 VHH antibody (4E6 monomer) at various concentrations was added thereto. The cells were further cultured overnight, 10 µl of a viable cell count reagent SF (Nacalai Tesque, Inc.) was added thereto, and the absorbance at 450 nm was measured after 2 hours of cultivation. The measured value of a cell-free medium in a well was subtracted as a background value. The values measured for the wells containing cells alone were designated 100%, and the relative values were determined. The results were shown as the mean plus the standard deviation of the results for 3 wells at each concentration. As shown in FIG. 11, apoptosis caused by TRAIL could not be inhibited by the 4P6 monomer or the 4E6 monomer alone. When the 4P6 monomer and the 4E6 monomer were added simultaneously, however, apoptosis was inhibited in a dose-dependent manner. Since hTRAIL, the 4P6 monomer, and the 4E6 monomer have substantially equivalent molecular weights, the VHH antibody at 100 ng/ml is substantially equal to hTRAIL at 100 ng/ml in terms of molar concentration. The results described above demonstrate that the 4P6 monomer and the 4E6 monomer not only bind to hTRAIL-R1 and hTRAIL-R2 on the cell surface but also act as antagonists.

As described above, a novel antibody (4P6) capable of specifically binding to hTRAIL-R1 and serving as an antagonist was obtained.

Example 6

Preparation of 4E6 Dimer Toxin, 4E6 Dimer EGFP, 4E6 Tetramer, and Recombinant *E. coli* BL21 (DE3) and Expression and Purification of the Recombinant Proteins (1) Preparation of Gene Expression Cassette
(1-1) Preparation of Gene Expression Cassette of Fusion Protein of Anti-hTRAIL-R2 VHH Antibody Dimer and *Pseudomonas aeruginosa* Exotoxin A Subunit (4E6 Dimer Toxin) to be Expressed in *E. coli*

Figure 15:
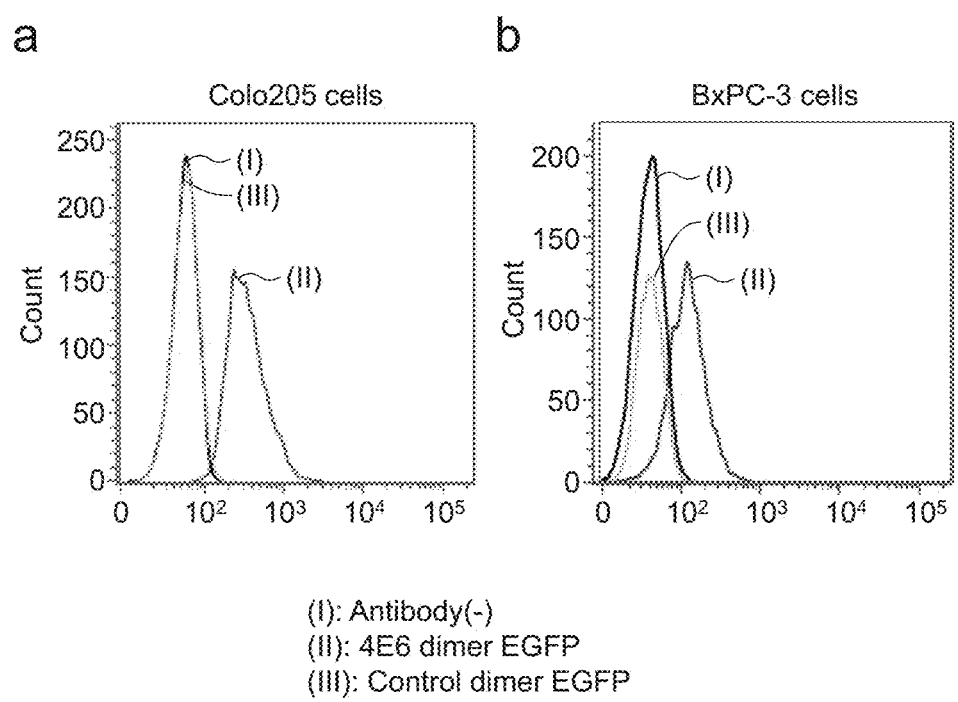
FIG. 15 shows fluorescent staining of cancer cells (a: Colo205 cells; and b: BxPC-3 cells) with the 4E6 dimer EGFP. The vertical axis indicates the cell count and the horizontal axis indicates the fluorescence intensity of the 4E6 dimer EGFP.

The 4E6 dimer toxin gene to be expressed in *E. coli* was amplified via PCR using the gene expression cassette (SEQ ID NO: 2) of 4E6 dimer toxin to be expressed in *Bifidobacterium* inserted into the pBluescriptII(+) plasmid as a template, and primers having the DNA sequence 5 (SEQ ID NO: 12) and the DNA sequence 6 (SEQ ID NO: 13). PCR was carried out using PrimeSTAR GXL DNA Polymerase (TAKARA BIO INC.) as DNA polymerase through a cycle of 95° C. for 1 minute and 25 cycles of 98° C. for 10 seconds, 60° C. for 15 seconds, and 68° C. for 2 minutes. The amplified product was purified using the MinElute column (Qiagen) in accordance with the attached protocols, digested with restriction enzymes NdeI and NotI, and subjected to 1.2% agarose gel electrophoresis. The band of interest was cleaved from the gel, followed by isolation and purification with the use of the DNA gel extraction kit (Qiagen) in accordance with the attached protocols. The resultant was inserted between the NdeI site and the NotI site of pET-22b(+) (Novagen), so as to construct the 4E6 dimer toxin comprising Strep-tag at its N terminus (Schmidt T. G., Skerra A., 2007, Nat. Protoc., 2 (6): 1528-1535), two VHH monomers linked with each other with the linker peptide (GGSGG)$_2$ (SEQ ID NO: 28), and the *Pseudomonas aerugi*- nosa exotoxin subunit A (toxin) linked to the C terminus of the 4E6 dimer through the XbaI sequence (SerArg) (FIG. 12*a*).

(1-2) Preparation of Gene Expression Cassette of Fusion Protein of Anti-hTRAIL-R2 VHH Antibody Dimer and Green Fluorescent Protein (4E6 Dimer EGFP) to be Expressed in *E. coli*

The 4E6 dimer EGFP gene to be expressed in *E. coli* was amplified via PCR using the gene expression cassette (SEQ ID NO: 3) of the 4E6 dimer toxin to be expressed in *Bifidobacterium* inserted into the pBluescriptII(+) plasmid as a template and primers having the DNA sequence 5 (SEQ ID NO: 12) and the DNA sequence 7 (SEQ ID NO: 14). PCR was carried out using PrimeSTAR GXL DNA Polymerase (TAKARA BIO INC.) as DNA polymerase through a cycle of 95° C. for 1 minute and 25 cycles of 98° C. for 10 seconds, 60° C. for 15 seconds, and 68° C. for 2 minutes. The amplified product was purified using the MinElute column (Qiagen) in accordance with the attached protocols, digested with restriction enzymes NdeI and NotI, and subjected to 1.2% agarose gel electrophoresis. The band of interest was cleaved from the gel, followed by isolation and purification with the use of the DNA gel extraction kit (Qiagen) in accordance with the attached protocols. The resultant was inserted between the NdeI site and the NotI site of pET-22b(+) (Novagen), so as to construct the 4E6 dimer EGFP comprising Strep-tag at its N terminus, two VHH monomers linked with each other with the linker peptide $(GGSGG)_2$ (SEQ ID NO: 28), and a green fluorescent protein (EGFP), to which the linker peptide $(GGSGG)_2$ (SEQ ID NO: 28) was bound to the N terminus, linked to the C terminus of the 4E6 dimer through the XbaI sequence (SerArg) (FIG. 12*b*).

(1-3) Preparation of Gene Expression Cassette of Anti-hTRAIL-R2 VHH Antibody Tetramer (4E6 Tetramer) to be Expressed in *E. coli*

The 4E6 tetramer gene to be expressed in *E. coli* was amplified via PCR using the gene expression cassette (SEQ ID NO: 1) of the 4E6 tetramer to be expressed in *Bifidobacterium* inserted into the pEX-K plasmid as a template and primers having the DNA sequence 3 (SEQ ID NO: 10) and the DNA sequence 4 (SEQ ID NO: 11). PCR was carried out using PrimeSTAR GXL DNA Polymerase (TAKARA BIO INC.), as DNA polymerase through a cycle of 95° C. for 1 minute and 25 cycles of 98° C. for 10 seconds, 60° C. for 15 seconds, and 68° C. for 2 minutes. The amplified product was purified using the MinElute column (Qiagen) in accordance with the attached protocols, digested with restriction enzymes NdeI and NotI, and subjected to 1.2% agarose gel electrophoresis. The band of interest was cleaved from the gel, followed by isolation and purification with the use of the DNA gel extraction kit (Qiagen) in accordance with the attached protocols. The resultant was inserted between the NdeI site and the NotI site of pET-22b (+) (Novagen), so as to construct the 4E6 tetramer comprising Strep-tag at its N terminus, four VHH monomers linked with each other with three linker peptides $(GGSGG)_2$ (SEQ ID NO: 28) (FIG. 12*c*).

(2) Expression of the Recombinant Proteins in *E. coli*

The 4E6 tetramer, the 4E6 dimer toxin, and the 4E6 dimer EGFP genes obtained as described above were inserted between the NdeI site and the NotI site of pET22b(+). This expression vector (plasmid DNA) was introduced into *E. coli* RosettaGami (DE3)2 (Novagen), recombinant *E. coli* cells were cultured using 200 ml of 2YT medium containing 100 μg/ml ampicillin (Sigma-Aldrich) at 37° C. in accordance with the attached instructions, and 1 mM IPTG (isopropyl-β-thiogalactopyranoside, TAKARA BIO INC.) was added when $OD_{600}$ reached 0.4 to 0.5, followed by cultivation at 30° C. for 3 hours. Following the cultivation, *E. coli* cells were recovered and resuspended in 20 ml of extraction buffer (50 mM Na phosphate, pH 7.8, 300 mM NaCl, EDTA-free protease inhibitor cocktail, Roche), and the cells were disrupted by ultrasonication on ice using Sonifier 250 (Branson) at the output control of 2 and the duty cycle of 80% for 1 minute twice. After the treatment, the suspension was centrifuged at 15,000 rpm and 4° C. for 20 minutes, and the supernatant was recovered. The fusion protein was purified using the HisTrap column (GE Healthcare). The centrifuged supernatant of the ultrasonicated suspension was directly applied to the HisTrap column, the column was washed with a binding buffer (20 mM Na phosphate, 0.5 M NaCl, 20 mM imidazole, pH 7.4), and the fusion protein was then eluted with an eluate containing 500 mM imidazole. The purified sample was subjected to 10% SDS-polyacrylamide gel electrophoresis and stained with CBB. The purified recombinant protein was observed, and the concentration of the target protein band was estimated by comparing with the results of staining of BSA (bovine serum albumin) (FIG. 13*a-c*). The estimated concentrations of the 4E6 dimer toxin, the 4E6 dimer EGFP, and the 4E6 tetramer were 0.8 mg/ml, 1.2 mg/ml, and 1.6 mg/ml, respectively.

Example 7

Measurement of Activity of 4E6 Dimer Toxin and 4E6 Tetramer to Induce Cancer Cell Apoptosis Whether or not the 4E6 dimer toxin fusion protein exerts activity of inducing apoptosis on cultured hTRAIL-R2-expressing human cancer cells (Colo205, obtained from American Type Culture Collection) was investigated. The cells were added to a Falcon 96-well culture plate (Becton, Dickinson and Company) at $5\times10^4$ cells/50 μl of medium (RPMI 1640 medium containing 0.2% fetal bovine serum (Tissue Culture Biologicals))/well, the cells were cultured for 2 hours, and then 50 μl each of media containing the 4E6 dimer toxin and the 4E6 dimer EGFP purified as described above was added to the final concentrations of 2,000, 800, 160, 32, 6.4, 1.28, 0.256, and 0.0512 ng/ml (2× final concentration), respectively. 10 μl of an MTT reagent (Nacalai Tesque, Inc.) was added, after cultivating for 2 days. The cells were then cultured for an additional 2 hours, a solubilizer was added at 100 μl/well, the cells were lysed by pipetting, and the absorbance at $OD_{570}$ nm was measured. The measured value of a cell-free medium in a well was subtracted as a background value from all the measured values. The values measured for the wells containing cells alone were designated 100%, and the relative values were determined. Assay was performed in triplicate, and an average value of the results for 3 wells was employed. As shown in FIG. 14*a*, a fusion construct comprising an anti-TRAIL-R2 VHH antibody dimer and Toxin; that is, Immunotoxin, did not induce apoptosis at all.

Whether or not the 4E6 dimer binds to the cells was examined as described below. Specifically, human colon cancer cells (Colo205 cells) and pancreatic cancer cells (BxPC-3 cells) ($2\times10^5$ each) were reacted in 50 μl of phosphate buffered saline (pH 7.4) containing 10 μg/ml 4E6 dimer EGFP and 2% fetal bovine serum on ice for 30 minutes. The cells were washed twice with the serum-containing phosphate buffered saline, and the fluorescent intensity of the cells was analyzed using the FACSVerse flow cytometer (BD Biosciences). Both cells were stained with the 4E6 dimer EGFP. In contrast, these cells were not stained with the control dimer EGFP (FIG. 15). Accordingly, the 4E6 dimer is considered to be able to bind to the cells.

According to the above results, the 4E6 dimer toxin binds to TRAIL-R2 on a cell membrane, but it does not allow TRAIL-R2 molecules to aggregate in a trimer or larger multimer, and the 4E6 dimer toxin is not incorporated into cells. Accordingly, the 4E6 dimer toxin was not considered to be able to induce apoptosis of Colo205 cells.

Figure 14:
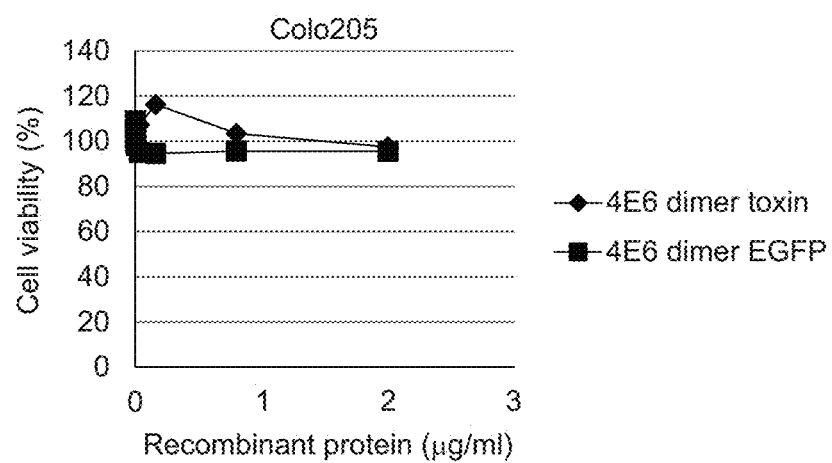
FIG. 14 shows activity of recombinant proteins (a: 4E6 dimer toxin and 4E6 dimer EGFP; and b: 4E6 monomer and 4E6 tetramer) to induce apoptosis of human colon cancer (Colo205) cells.
Figure 14:
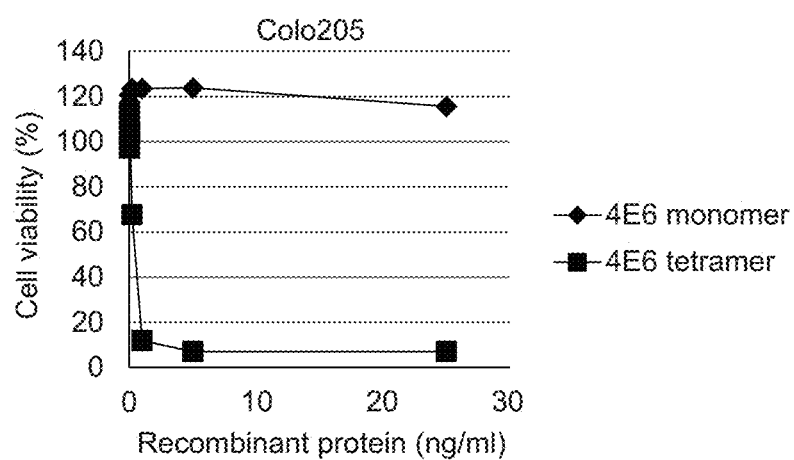

In order to examine whether or not the 4E6 monomer and the 4E6 tetramer exerts activity of inducing apoptosis, subsequently, 50 µl each of media containing the 4E6 monomer and the 4E6 tetramer purified as described above was added at final concentrations of 25,000, 5,000, 1,000, 200, 40, 8, 1.6, and 0.32 µg/ml (2× final concentration). As a result, the 4E6 monomer did not induce apoptosis, but the 4E6 tetramer having activity of aggregating TRAIL-R2 molecules in a trimer or larger multimer induced strong apoptosis of Colo205 cells (FIG. 14b).

The above results demonstrate that the anti-hTRAIL-R VHH antibody tetramer having activity of aggregating TRAIL-R molecules in a trimer or larger multimer induces cancer cell apoptosis more efficiently than the anti-hTRAIL-R VHH antibody dimer toxin.

Example 8

Figure 16:
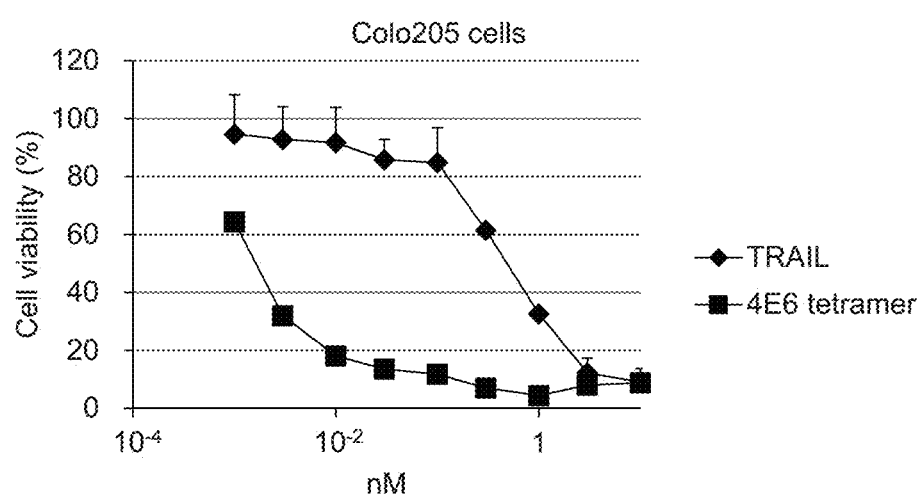
FIG. 16 shows activity of the anti-hTRAIL-R2 VHH antibody tetramer (4E6 tetramer) expressed in $E.\ coli$ to induce apoptosis of human colon cancer (Colo205) cells (a) and pancreatic cancer (BxPC-3) cells (b).
Figure 16:
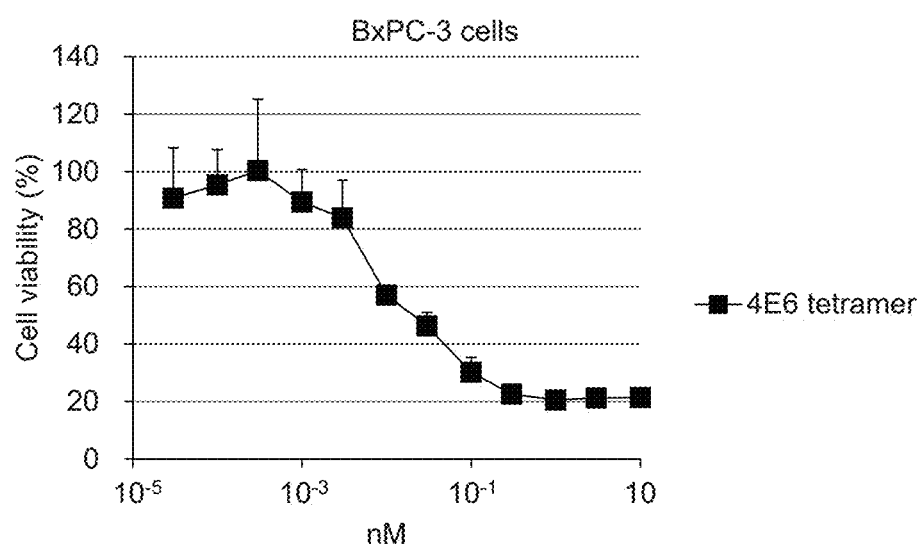

Activity of 4E6 Tetramer Expressed in *E. coli* to Induce Apoptosis of Human Colon Cancer Cells and Pancreatic Cancer Cells Activity of the 4E6 tetramer to induce cancer cell apoptosis of human colon cancer cells (Colo205 cells) and pancreatic cancer cells (BxPC-3 cells) (obtained from American Type Culture Collection) was examined. The cells were suspended in RPMI 1640 medium (Sigma) supplemented with 10% fetal bovine serum (Tissue Culture Biologicals), the cells were added to a Falcon 96-well culture plate (Becton, Dickinson and Company) at $3\times10^3$ cells/50 µl/well, the cells were cultured overnight, and 50 µl each of media containing the 4E6 tetramer or hTRAIL (Wako Pure Chemical Industries, Ltd.) was then added. Colo205 cells were cultured overnight for a day, BxPC-3 cells were overnight for two days, 10 µl of a viable cell count reagent SF (Nacalai Tesque, Inc.) was added, the cells were cultured for an additional 4 to 6 hours, and the absorbance at 450 nm was then measured. The measured value of a cell-free medium in a well was subtracted as a background value. The values measured for the wells containing cells alone were designated 100%, and the relative values were determined. The results were shown as the mean plus the standard deviation of the results for 3 wells at each concentration. As shown in FIG. 16, the 4E6 tetramer induced apoptosis of Colo205 and BxPC-3 cells in a concentration-dependent manner, and the $IC_{50}$ values were 2 pmol/l and 8 pmol/l, respectively. The $IC_{50}$ value of hTRAIL prepared using *E. coli* was 400 pmol/l, and the 4E6 tetramer was found to be able to induce apoptosis at a concentration lower than that of hTRAIL.

Example 9

Expression and Secretion of 4E6 Tetramer and 4E6 Dimer EGFP in *Bifidobacterium* and Purification Thereof (1) Preparation of Recombinant *Bifidobacterium* Via Electroporation The vector gene cassette for secretion and expression of the 4E6 tetramer and the 4E6 dimer EGFP in *Bifidobacterium* (see Example 1) was inserted between HindIII and NotI of the pKKT427 vector (Yasui K., et al., Nucleic Acids Res., 2009), and the resultant was introduced into *B. longum* 105-A via electroporation. Electroporation was carried out under conditions of 2.4 kV, 25 µf, and 200 ohms.

(2) Purification of 4E6 Tetramer and 4E6 Dimer EGFP Expressed and Secreted in *Bifidobacterium*

Figure 17:
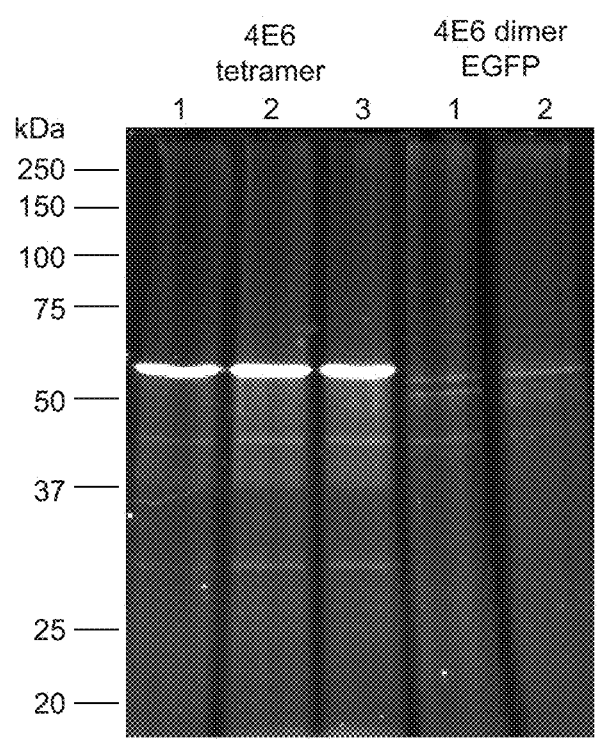
FIG. 17 shows SDS-PAGE images for the 4E6 tetramer and the 4E6 dimer EGFP purified from 1 ml of the culture supernatant of $Bifidobacterium$. The results for the 4E6 tetramer are obtained from 3 clones and the results for the 4E6 dimer EGFP are obtained from 2 clones.

The recombinant *Bifidobacterium* obtained in the above (1) was added to MRS liquid medium (Lactobacilli MRS Broth, Difco Laboratories, Detroit, Mich.) containing 100 µg/ml spectinomycin supplemented with 50 mM sucrose, 3.4 mg/ml L-ascorbic acid sodium salt, and 0.2 mg/ml L-cysteine hydrochloride, and the cells were cultured anaerobically overnight. The cells were cultured anaerobically with the use of a sealed container containing a deoxidizer, Anaero Pack Kenki (Mitsubishi Gas Chemical Company, Inc., Tokyo, Japan). After cultivating overnight, the absorbance at 600 nm the culture solution was measured, and the culture solution was added to a fresh liquid medium, so as to adjust the absorbance to 0.1. The cells were cultured anaerobically for 6 to 7 hours, the culture supernatant was collected by centrifugation at 4° C. and 9,400×g for 10 minutes. The recombinant protein was purified using the HisTrap column (GE Healthcare). The culture supernatant was applied to the HisTrap column, the column was washed with a binding buffer (50 mM Na phosphate, 0.3 M NaCl, 20 mM imidazole, pH 7.8), and the protein was then eluted with an eluate containing 500 mM imidazole. The purified protein obtained from 1 ml of the culture supernatant was subjected to SDS polyacrylamide gel electrophoresis and then stained with Oriole Fluorescent Gel Stain (Bio-Rad) (FIG. 17). Both the 4E6 tetramer and the 4E6 dimer EGFP were detected around the deduced molecular weight (about 60 kDa). The amount of the 4E6 tetramer secreted in the culture supernatant was estimated to be 400 ng/ml, and that of the 4E6 dimer EGFP was estimated to be 3.2 ng/ml. The results demonstrate that both the recombinant proteins were secreted and that the 4E6 tetramer was more efficiently expressed and secreted than the 4E6 dimer EGFP.

Example 10

Figure 18:
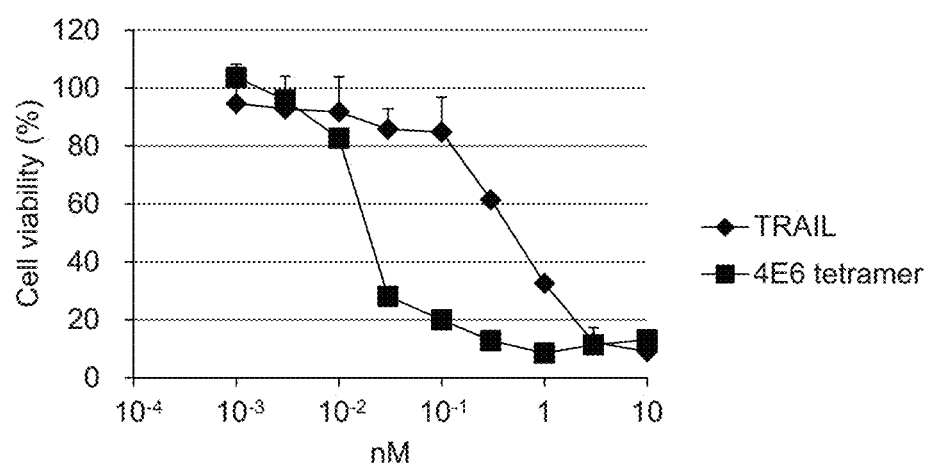
FIG. 18 shows activity of the 4E6 tetramer purified from the culture supernatant of $Bifidobacterium$ to induce apoptosis of Colo205 cancer cells.

Activity of Anti-hTRAIL-R2 VHH Antibody Tetramer (4E6 Tetramer) Expressed and Secreted in *Bifidobacterium* to Induce Cancer Cell Apoptosis Activity of the 4E6 tetramer to induce cancer cell apoptosis of human colon cancer cells (Colo205 cells) (American Type Culture Collection) was examined. The cells were suspended in RPMI 1640 medium (Sigma) supplemented with 10% fetal bovine serum (Tissue Culture Biologicals), and the cells were added to a Falcon 96-well culture plate (Becton, Dickinson and Company) at $3\times10^3$ cells/50 µl medium/well. The cells were cultured overnight, and 50 µl each of media containing the 4E6 tetramer or TRAIL at the final concentration of 0.3 pM to 10 nM was added thereto. The cells were further cultured overnight, 10 µl of a viable cell count reagent SF (Nacalai Tesque, Inc.) was added thereto, the cells were cultured for 6 hours, and the absorbance at 450 nm was measured. The measured value of a cell-free medium in a well was subtracted as a background value. The values measured for the wells containing cells alone were designated 100%, and the relative values were determined. The results were shown as the mean plus the standard deviation of the results for 3 wells at each concentration. As shown in FIG. 18, the 4E6 tetramer inhibited the growth of the Colo205 cells in a concentration-dependent manner, and the $IC_{50}$ value was 0.02 nmol/l. Meanwhile, the $IC_{50}$ value of hTRAIL (Wako Pure Chemical Industries, Ltd.) prepared in *E. coli* was 0.4 nmol/l. Thus, the 4E6 tetramer expressed and secreted in *Bifidobacterium* was found to have higher activity to induce apoptosis than hTRAIL.

Example 11

Figure 19:
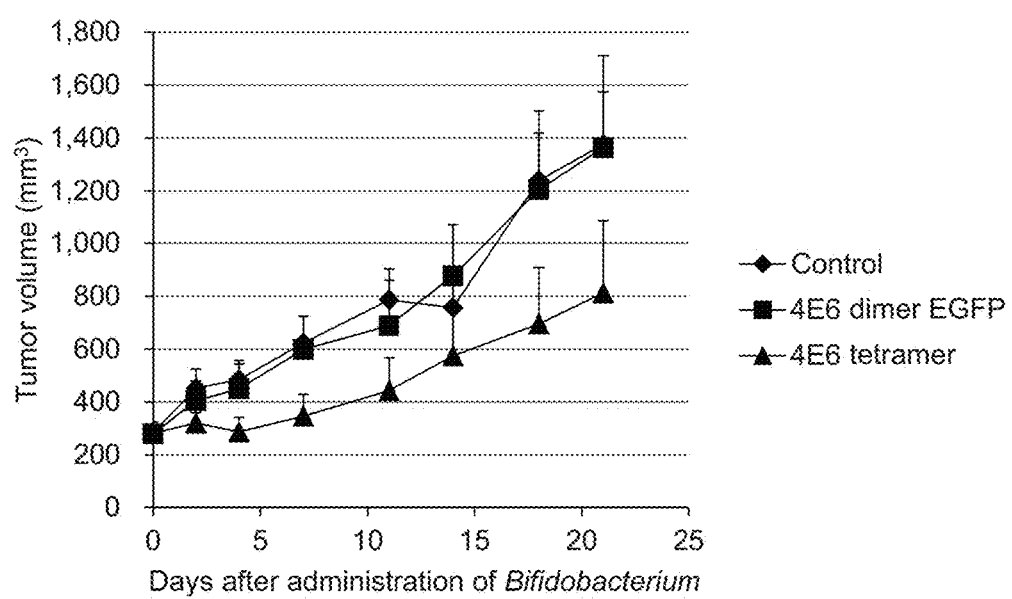
FIG. 19 shows the antitumor effects of the 4E6 tetramer-secreting $Bifidobacterium$ in nude mice into which Colo205 cells were transplanted. The tumor volume ($mm^3$) is shown as the mean+standard error (n=6).

Examination of Antitumor Effect of Recombinant
*B. longum* Via Intravenous Administration in
Xenograft Model Transplanted with Colo205 Cells Antitumor effects of recombinant *B. longum* 105-A cells expressing and secreting the anti-hTRAIL-R2 VHH antibody tetramer (4E6 tetramer) were examined when the recombinant *B. longum* 105-A cells were administered intravenously to xenograft models prepared by transplanting human colon cancer cells (Colo205 cells) subcutaneously into nude mice to form solid cancer. Specifically, $2 \times 10^6$ Colo205 cells were transplanted subcutaneously into 6-week-old female KSN/Slc nude mice, and 9 days later, the mice were divided into groups (n=6; control, 4E6 tetramer, and 4E6 dimer EGFP groups) so as to adjust the tumor mass volume of each group to approximately 280 mm³, and the recombinant *Bifidobacterium* prepared in accordance with Example 9 were administered intravenously at $1.5 \times 10^9$ cells/mouse. The *B. longum* 105-A used was prepared via centrifugation and resuspension with saline. For nutritional supplementation of *B. longum* 105-A in the body, 1 ml of 20% lactulose was intraperitoneally administered every day. The tumor size was measured with the use of a caliper 0, 2, 4, 7, 11, 14, 18, and 21 days after *Bifidobacterium* administration. The tumor volume was determined by the formula: (shorter diameter)²×(longer diameter)/2. The results are shown in FIG. 19. In comparison with the control group, the tumor growth was inhibited by 51% 21 days after administrating the recombinant *Bifidobacterium* expressing and secreting the 4E6 tetramer. On the other hand, the inhibitory effects of tumor growth were not observed, in the negative control group to which *Bifidobacterium* secreting the 4E6 dimer EGFP had been administered.

Figure 20:
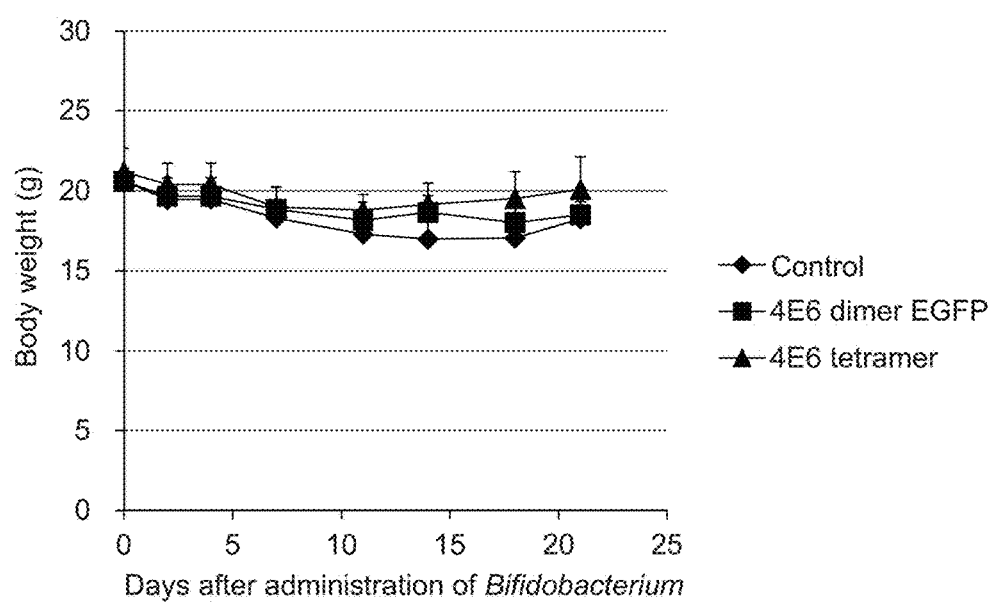
FIG. 20 shows changes in the body weight of nude mice into which Colo205 cells were transplanted upon administration of 4E6 tetramer-secreting $Bifidobacterium$. The body weight is shown as the mean+standard deviation (n=6).

Together with measuring the tumor size, body weights of all groups were measured at 0, 2, 4, 7, 11, 14, 18, and 21 days after *Bifidobacterium* administration. As shown in FIG. 20, body weight loss was not detected in the 4E6 tetramer group, in comparison with the control group and the 4E6 dimer EGFP group. On the basis of the results described above, the 4E6 tetramer is considered to inhibit tumor growth by apoptosis-inducing activity without causing side effects such as body weight loss.

Example 12

Figure 21:
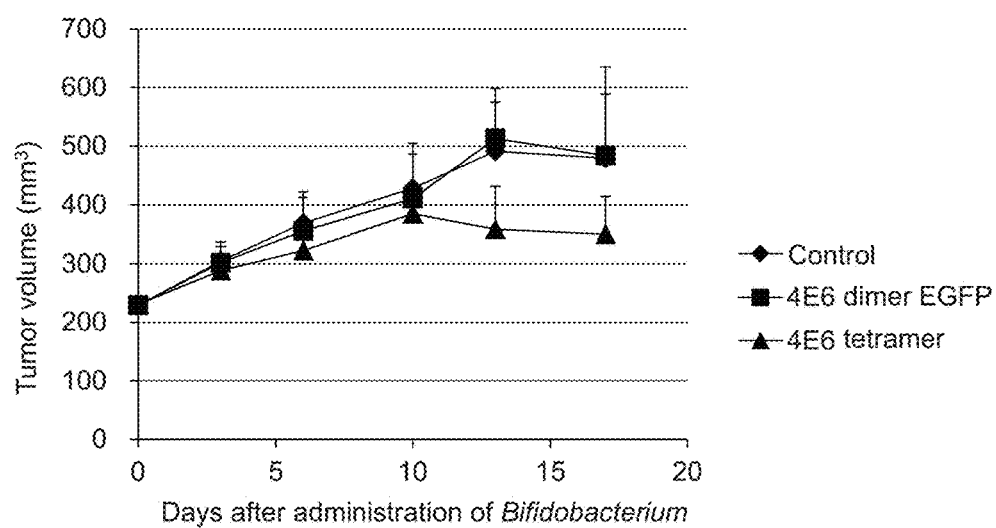
FIG. 21 shows the antitumor effects of 4E6 tetramer-secreting $Bifidobacterium$ in nude mice into which BxPC-3 cells were transplanted. The tumor volume ($mm^3$) is shown as the mean+standard error (n=6).

Examination of Antitumor Effect of Recombinant
*B. longum* Via Intravenous Administration in
Xenograft Model Transplanted with BxPC-3 Cells Antitumor effects of recombinant *B. longum* 105-A cells expressing and secreting the anti-hTRAIL-R2 VHH antibody tetramer (4E6 tetramer) were examined when the recombinant *B. longum* 105-A cells were administered intravenously to xenograft models prepared by transplanting human pancreatic cancer cells (BxPC-3 cells) subcutaneously into nude mice to form solid cancer. Specifically, $2 \times 10^6$ BxPC-3 cells were transplanted subcutaneously into 8-week-old female KSN/Slc nude mice, and 8 days later, the mice were divided into groups (n=6; control, 4E6 tetramer, and 4E6 dimer EGFP groups) so as to adjust the tumor mass volume of each group to approximately 230 mm³, and the recombinant *Bifidobacterium* cells prepared in accordance with Example 9 were administered intravenously at $1.5 \times 10^9$ cells/mouse. The *B. longum* 105-A used was prepared via centrifugation and resuspension with saline. For nutritional supplementation of *B. longum* 105-A in the body, 1 ml of 20% lactulose was intraperitoneally administered every day. The tumor size was measured with the use of a caliper 0, 3, 6, 10, 13, and 17 days after *Bifidobacterium* administration. The tumor volume was determined by the formula: (shorter diameter)²×(longer diameter)/2. The results are shown in FIG. 21. The tumor growth was inhibited by 52% 17 days after administrating the recombinant *Bifidobacterium* expressing and secreting the 4E6 tetramer, in comparison with the control group. The inhibitory effects of tumor growth were not observed in the negative control group to which *Bifidobacterium* secreting the 4E6 dimer EGFP had been administered.

Figure 22:
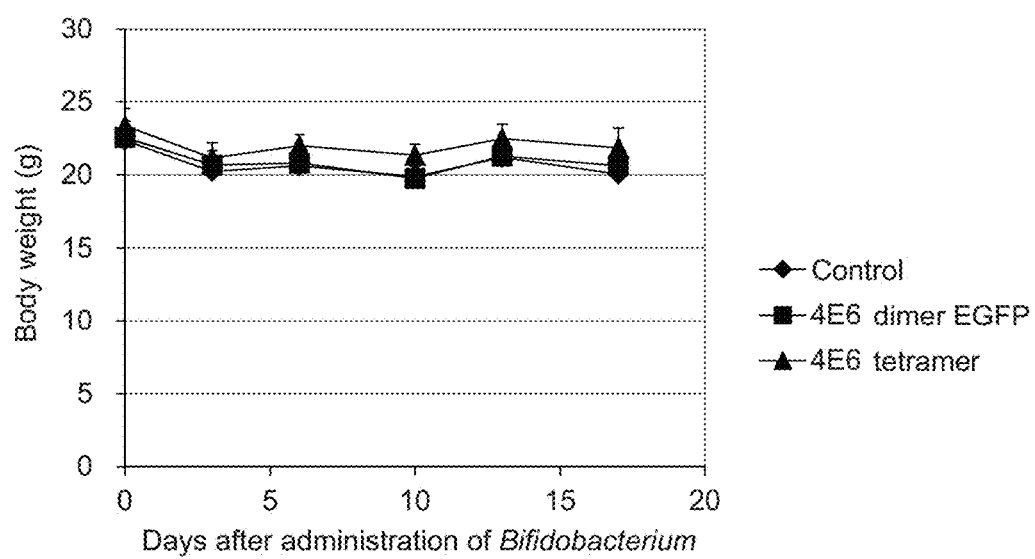
FIG. 22 shows changes in the body weight of nude mice into which BxPC-3 cells were transplanted upon administration of 4E6 tetramer-secreting $Bifidobacterium$. The body weight is shown as the mean+standard deviation (n=6).

Together with measuring the tumor size, body weights of all groups were measured at 0, 3, 6, 10, 13, and 17 days after *Bifidobacterium* administration. As shown in FIG. 22, body weight loss was not detected in the 4E6 tetramer group, in comparison with the control group and the 4E6 dimer EGFP group. On the basis of the results described above, the 4E6 tetramer is considered to inhibit tumor growth by apoptosis-inducing activity without causing side effects such as body weight loss.

Example 13

Preparation of 4P6 Trimer Recombinant *E. coli*
BL21 (DE3) and Expression and Purification of
Recombinant Proteins (1) Preparation of Gene Expression Cassette of Anti-hTRAIL-R1 VHH Antibody Trimer (4P6 Trimer) to be Expressed in *E. coli*

A gene encoding a 4P6 trimer comprising Strep-tag at its N terminus and the His-Tag sequence at its C terminus and 3 monomers of the anti-hTRAIL-R1 VHH antibody obtained in accordance with Example 4 (1) linked with two linker peptides $(GGSGG)_2$ (SEQ ID NO: 28) was inserted between the NdeI site and the NotI site of pET-22b(+) (Novagen), so as to construct a 4P6 trimer gene expression cassette to be expressed in *E. coli* (see Example 6).

(2) Expression of Recombinant Protein in *E. coli*

Figure 23:
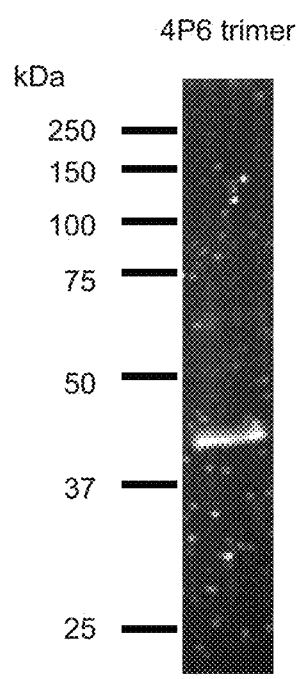
FIG. 23 shows an SDS-PAGE image for the purified recombinant protein (4P6 trimer) expressed in $E.\ coli$.

The plasmid vector prepared as described above was introduced into *E. coli* BL21Star™ (DE3) One Shot (Life Technologies). In accordance with the attached instructions, recombinant *E. coli* cells were cultured in 200 ml of 2YT medium containing 100 µg/ml ampicillin (Sigma-Aldrich) at 37° C., and 1 mM IPTG (isopropyl-β-thiogalactopyranoside, TAKARA BIO INC.) was added thereto when $OD_{600}$ reached 0.4 to 0.5, followed by cultivation at 30° C. for 3 hours. Following the cultivation, *E. coli* cells were recovered and resuspended in 20 ml of an extraction buffer (50 mM Na phosphate, pH 7.8, 300 mM NaCl, EDTA-free protease inhibitor cocktail, Roche). The cells were disrupted by ultrasonication on ice using Sonifier 250 (Branson) at the output control of 2 and the duty cycle of 80% for 1 minute twice. The supernatant was recovered by centrifuging the treated suspension at 9,400×g and 4° C. for 20 minutes. The fusion protein was purified with the use of the HisTrap column (GE Healthcare, U.K.). The centrifuged supernatant of the ultrasonicated suspension was applied directly to the HisTrap column, the column was washed with a binding buffer (20 mM sodium phosphate, 0.5 M NaCl, 20 mM imidazole, pH 7.4), and the fusion protein was then eluted with the use of an eluate containing 500 mM imidazole. Further, the elusion fraction was applied to the Strep-Tactin column (IBA) and purified in accordance with the attached instructions. The purified protein in an amount equivalent to 50 ng of BSA was subjected to SDS polyacrylamide gel electrophoresis and then stained with Oriole Fluorescent Gel Stain (Bio-Rad) (FIG. 23). The 4P6 trimer was detected around the deduced molecular weight (about 42 kDa). The results demonstrate that the 4P6 trimer can be expressed in *E. coli* and purified.

Example 14

Figure 24:
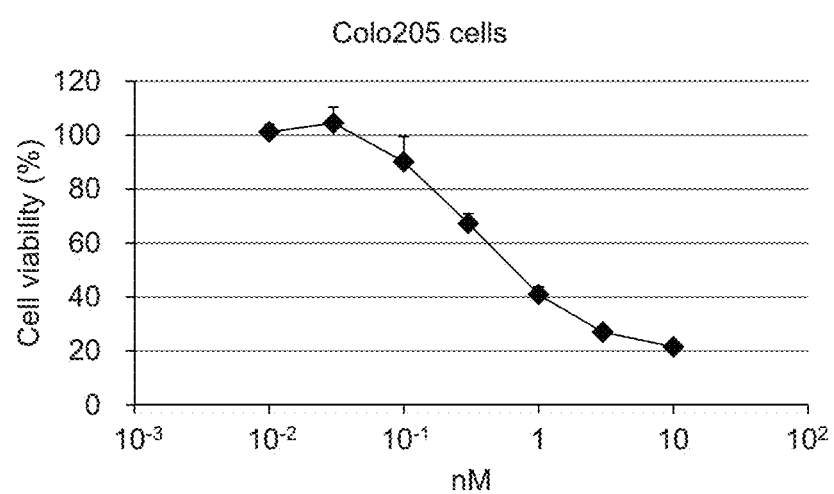
FIG. 24 shows activity of the anti-hTRAIL-R1 VHH antibody trimer (4P6 trimer) expressed in $E.\ coli$ to induce apoptosis of human colon cancer (Colo205) cells.

Measurement of Activity of 4P6 Trimer Expressed in *E. coli* to Induce Cancer Cell Apoptosis Activity of the 4P6 trimer to induce cancer cell apoptosis of human colon cancer cells (Colo205 cells) (American Type Culture Collection) was examined. The cells were suspended in RPMI 1640 medium (Sigma) supplemented with 10% fetal bovine serum (Tissue Culture Biologicals), and the cells were added to a Falcon 96-well culture plate (Becton, Dickinson and Company) at $3\times10^3$ cells/50 µl medium/well. The cells were cultured overnight, and 50 µl each of media containing the 4P6 trimer at the final concentration of 10 pM to 10 nM was added thereto. The cells were further cultured overnight for two days, 10 µl of a viable cell count reagent SF (Nacalai Tesque, Inc.) was added thereto, the cells were cultured for 4 hours, and the absorbance at 450 nm was measured. The measured value of a cell-free medium in a well was subtracted as a background value. The values measured for the wells containing cells alone were designated 100%, and the relative values were determined. The values were shown as the mean plus the standard deviation of the results for 3 wells at each concentration. As shown in FIG. 24, the 4P6 trimer inhibited the growth of the Colo205 cells in a concentration-dependent manner, and the $IC_{50}$ value was 0.4 nmol/l. The $IC_{50}$ value of hTRAIL prepared in *E. coli* (Wako Pure Chemical Industries, Ltd.) was 0.4 nmol/l, and the 4P6 trimer expressed in *E. coli* exerted activity of inducing apoptosis at the similar level as that of hTRAIL.

Example 15

Expression and Secretion of Anti-hTRAIL-R1 VHH Antibody Trimer (4P6 Trimer) in *Bifidobacterium* and Purification Thereof (1) Preparation of Recombinant *Bifidobacterium* Via Electroporation The vector gene cassette for expression and secretion of the 4P6 trimer in *Bifidobacterium*, which was prepared by replacing the 4E6 tetramer portion in the expression cassette prepared in Example 1 (1) with the 4P6 trimer obtained in accordance with Example 4 (1), was inserted between HindIII and NotI of the pKKT427 vector (Yasui K., et al., Nucleic Acids Res., 2009), and the resultant was introduced into *B. longum* 105-A via electroporation. Electroporation was carried out under conditions of 2.4 kV, 25 µf, and 200 ohms.

(2) Purification of 4P6 Trimer Expressed and Secreted in *Bifidobacterium*

Figure 25:
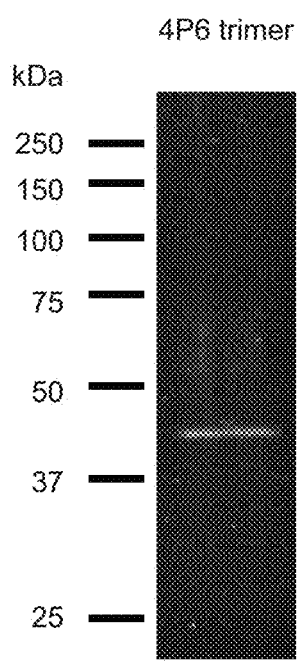
FIG. 25 shows an SDS-PAGE image for the 4P6 trimer purified from the culture supernatant of $Bifidobacterium$.

The recombinant *Bifidobacterium* obtained in the above (1) was added to MRS liquid medium containing 100 µg/ml spectinomycin (Lactobacilli MRS Broth, Difco Laboratories, Detroit, Mich.) supplemented with 50 mM sucrose, 3.4 mg/ml L-ascorbic acid sodium salt, and 0.2 mg/ml L-cysteine hydrochloride, and the cells were cultured anaerobically overnight. The cells were cultured anaerobically with the use of a sealed container containing a deoxidizer, Anaero Pack Kenki (Mitsubishi Gas Chemical Company, Inc., Tokyo, Japan). Following cultivating overnight, the absorbance at 600 nm of the culture solution was measured, and the culture solution was added to a fresh liquid medium, so as to adjust the absorbance to 0.1. The cells were cultured anaerobically for 7 hours, and the culture supernatant was then collected by centrifuging the culture medium at 4° C. and 9,400×g for 10 minutes. The recombinant protein was purified using the HisTrap column (GE Healthcare). The culture supernatant was applied to the HisTrap column, the column was washed with a binding buffer (50 mM Na phosphate, 0.3 M NaCl, 20 mM imidazole, pH 7.8), and the protein was then eluted with an eluate containing 500 mM imidazole. The purified protein obtained from 0.6 ml of the culture supernatant was subjected to SDS polyacrylamide gel electrophoresis and then stained with Oriole Fluorescent Gel Stain (Bio-Rad) (FIG. 25). The 4P6 trimer was detected around the deduced molecular weight (approximately 42 kD). As a result of quantification with the use of BSA, the amount of the 4P6 trimer secreted in the culture supernatant was estimated to be 30 ng/ml. The results demonstrate that the 4P6 trimer would be expressed and secreted in *Bifidobacterium*.

Example 16

Figure 26:
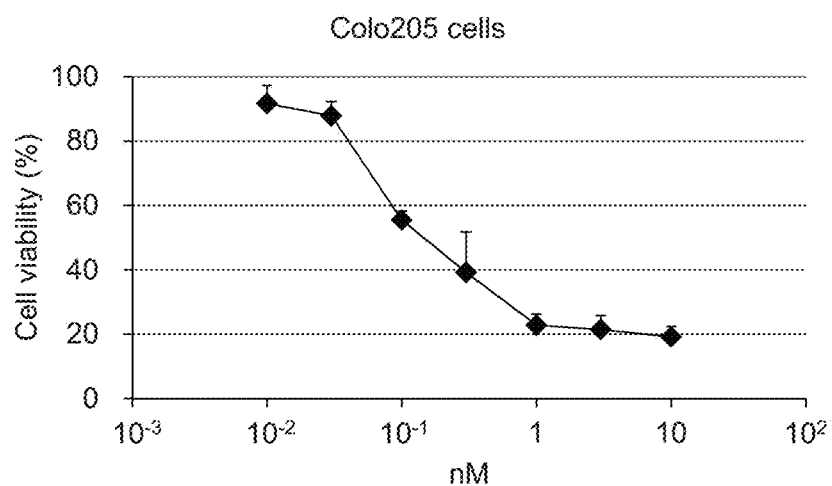
FIG. 26 shows activity of the anti-hTRAIL-R1 VHH antibody trimer (4P6 trimer) purified from the culture supernatant of $Bifidobacterium$ to induce apoptosis of human colon cancer (Colo205) cells (a) and pancreatic cancer (BxPC-3) cells (b).
Figure 26:
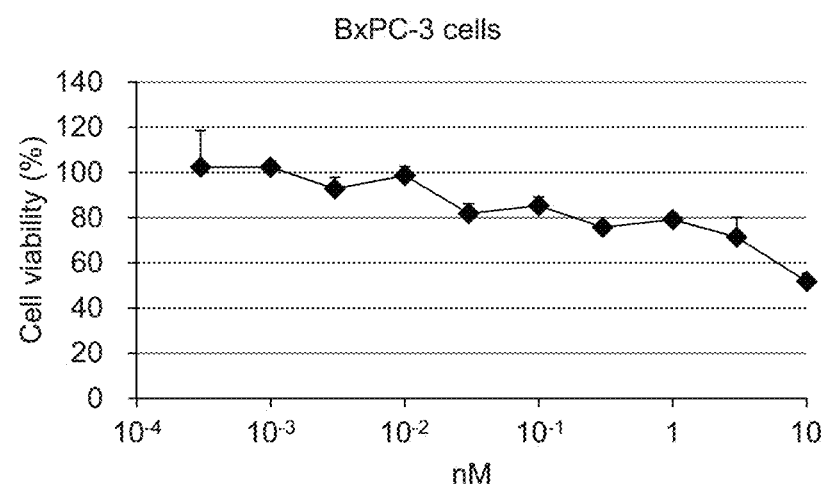

Activity of Anti-hTRAIL-R1 VHH Antibody Trimer (4P6 Trimer) Expressed and Secreted in *Bifidobacterium* to Induce Cancer Cell Apoptosis Activity of the 4P6 trimer to induce cancer cell apoptosis of human colon cancer cells (Colo205 cells) (American Type Culture Collection) and pancreatic cancer cells (BxPC-3 cells) (American Type Culture Collection) was examined. The cells were suspended in RPMI 1640 medium (Sigma) supplemented with 10% fetal bovine serum (Tissue Culture Biologicals), and the cells were added to a Falcon 96-well culture plate (Becton, Dickinson and Company) at $3\times10^3$ cells/50 µl medium/well. The cells were cultured overnight, and 50 µl each of media containing the 4P6 trimer at the final concentration of 0.3 pM to 10 nM was added thereto. The cells were further cultured overnight for two days, 10 µl of a viable cell count reagent SF (Nacalai Tesque, Inc.) was added thereto, the cells were cultured for 2 hours, and the absorbance at 450 nm was measured. The measured value of a cell-free medium in a well was subtracted as a background. The values measured for the wells containing cells alone were designated 100%, and the relative values were determined. The results were shown as the mean plus the standard deviation of the results for 3 wells at each concentration. As shown in FIG. 26a, the 4P6 trimer inhibited the growth of Colo205 cells in a concentration-dependent manner, and the $IC_{50}$ value was 0.08 nmol/l. The $IC_{50}$ value of hTRAIL (Wako Pure Chemical Industries, Ltd.) prepared in *E. coli* was 0.4 nmol/l, and the 4P6 trimer expressed and secreted in *Bifidobacterium* was found to have higher activity to induce apoptosis than hTRAIL. As shown in FIG. 26b, the 4P6 trimer also inhibited the growth of BxPC-3 cells in a concentration-dependent manner.

Example 17

**Examination of Antitumor Effect of Recombinant *B. longum* Expressing and Secreting 4P6 Trimer Via Intravenous Administration in Xenograft Model Transplanted with BxPC-3-Luc#2 Cells**

Figure 27:
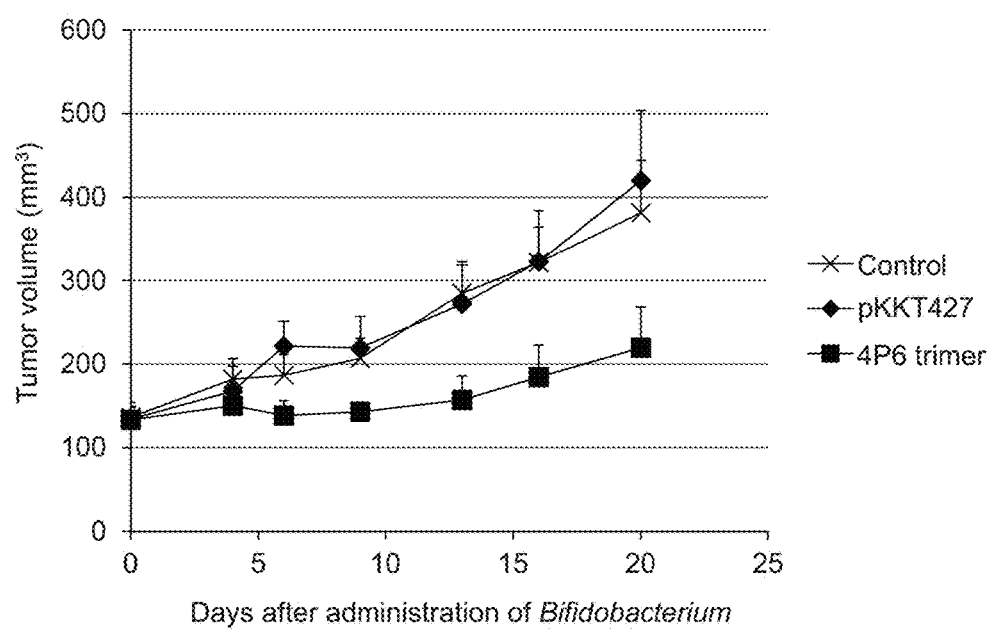
FIG. 27 shows antitumor effects of 4P6 trimer-secreting $Bifidobacterium$ in nude mice into which BxPC-3-Luc#2 cells were transplanted. The tumor volume ($mm^3$) is shown as the mean+standard error (n=5).

Antitumor effects of recombinant *B. longum* 105-A cells expressing and secreting the anti-hTRAIL-R1 VHH antibody trimer (4P6 trimer) were examined when the recombinant *B. longum* 105-A cells were administered intravenously to xenograft models prepared by transplanting human pancreatic cancer cells (BxPC-3-Luc#2 cells, obtained from JCRB Cell Bank) subcutaneously into nude mice to form solid cancer. Specifically, $3 \times 10^6$ BxPC-3-Luc#2 cells were transplanted subcutaneously into 6-week-old female KSN/Slc nude mice, and 15 days later, the mice were divided into groups (n=5; the control, the 4P6 trimer, and the pKKT427 vector groups) so as to adjust the tumor mass volume of each group to approximately 135 mm$^3$, and the recombinant *Bifidobacterium* cells prepared in accordance with Example 15 were administered intravenously at $3 \times 10^8$ cells/mouse. The *B. longum* 105-A used was prepared via centrifugation and resuspension with saline. For nutritional supplementation of *B. longum* 105-A in the body, 1 ml of 20% lactulose was intraperitoneally administered every day. The tumor size was measured with the use of a caliper 15, 19, 21, 24, 28, 31, and 35 days after tumor transplantation. The tumor volume was determined by the formula: (shorter diameter)$^2 \times$(longer diameter)/2. The results are shown in FIG. 27. The tumor growth was inhibited by 65% 20 days after administrating the recombinant *Bifidobacterium* expressing and secreting the 4P6 trimer, in comparison with the control group. The inhibitory effects of tumor growth were not observed in the negative control group to which pKKT427-introduced *Bifidobacterium* had been administered.

Figure 28:
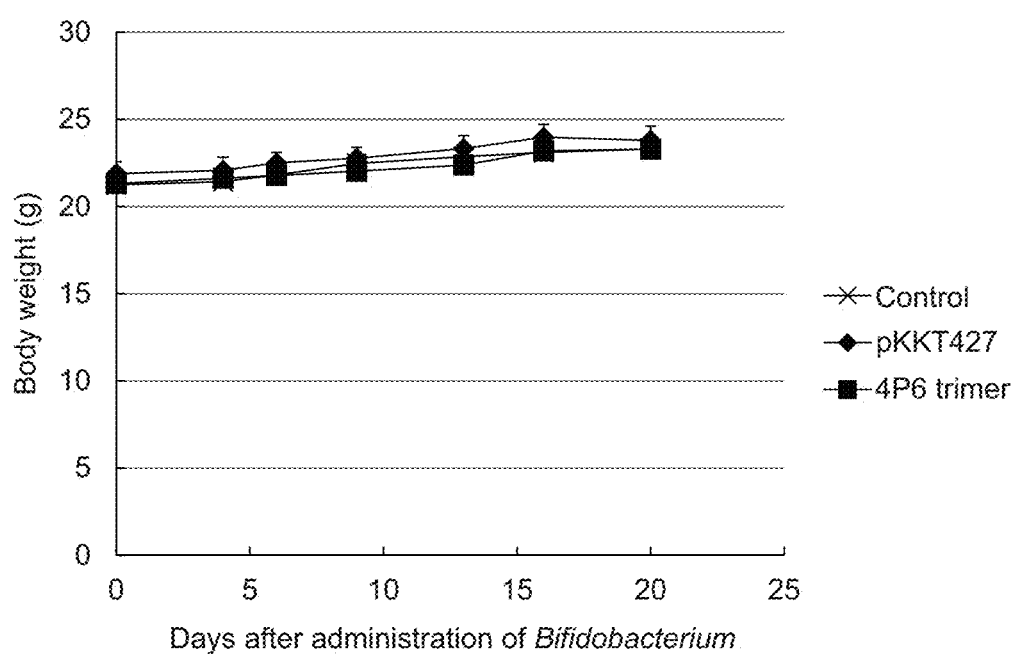
FIG. 28 shows changes in the body weight of nude mice into which BxPC-3-Luc#2 cells were transplanted upon administration of 4P6 trimer-secreting $Bifidobacterium$. The body weight is shown as the mean+standard error (n=5).

Together with measuring the tumor size, body weights of all groups were measured at 15, 19, 21, 24, 28, 31, and 35 days after tumor transplantation. As shown in FIG. 28, body weight loss was not detected in the 4P6 trimer group in comparison with the control group and the pKKT427-introduced *Bifidobacterium* group. On the basis of the results described above, the 4P6 trimer is considered to inhibit tumor growth by apoptosis-inducing activity without causing side effects such as body weight loss.

INDUSTRIAL APPLICABILITY

According to the present invention, cancer cell apoptosis can be effectively induced via topical application of the anti-hTRAIL-R1 antibody(ies) and the anti-hTRAIL-R2 antibody(ies) having potent agonistic activity into the tumor site while reducing the toxicity imposed on normal cells.

All publications, patents, and patent applications cited herein are incorporated herein by reference in their entirety.

---

The invention claimed is:

1. A recombinant obligate anaerobic Gram-positive bacteria comprising a nucleic acid encoding a fusion protein comprising a signal peptide and 3 or more anti-TRAIL-R1 single-chain antibodies and/or 3 or more anti-TRAIL-R2 single-chain antibodies, in an expressible state; wherein each of the 3 or more anti-TRAIL-R1 single-chain antibodies comprises CDR1 comprising the amino acid sequence of SEQ ID NO: 22; CDR2 comprising the amino acid sequence of SEQ ID NO: 23; and CDR3 comprising the amino acid sequence of SEQ ID NO: 24.

2. The recombinant obligate anaerobic Gram-positive bacteria of claim 1, wherein the obligate anaerobic Gram-positive bacteria belong to the genus *Bifidobacterium*.

3. The recombinant obligate anaerobic Gram-positive bacteria of claim 1, wherein each of the 3 or more anti-TRAIL-R2 single-chain antibodies comprises CDR1 comprising the amino acid sequence of SEQ ID NO: 15, CDR2 comprising the amino acid sequence of SEQ ID NO: 16, and CDR3 comprising the amino acid sequence of SEQ ID NO: 17.

4. The recombinant obligate anaerobic Gram-positive bacteria of claim 1, wherein the fusion protein further comprises one or more functional peptides.

5. The recombinant obligate anaerobic Gram-positive bacteria of claim 4, wherein the functional peptides comprise a labeling protein.

6. An antitumor agent comprising, as an active ingredient, the recombinant obligate anaerobic Gram-positive bacteria of claim 1, and one or more of a pharmaceutically acceptable excipient, emulsifier, suspension, surfactant, stabilizer and pH adjusting agent.

7. An anti-TRAIL-R1 antibody comprising CDR1, CDR2 and CDR3, wherein CDR1 comprises the amino acid sequence of SEQ ID NO: 22, CDR2 comprises the amino acid sequence of SEQ ID NO: 23 and CDR3 comprises the amino acid sequence of SEQ ID NO: 24.

8. The recombinant obligate anaerobic Gram-positive bacteria of claim 1, wherein the encoded fusion protein comprises a signal peptide, and 3 anti-TRAIL-R1 single-chain antibodies and/or 3 anti-TRAIL-R2 single-chain antibodies.

* * * * *